(12) United States Patent
Cardone et al.

(10) Patent No.: US 7,083,938 B2
(45) Date of Patent: *Aug. 1, 2006

(54) CELL-BASED SCREENING METHODS

(75) Inventors: Michael H. Cardone, Boston, MA (US); Michael Yaffe, Jamaica Plain, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 103 days.

This patent is subject to a terminal disclaimer.

(21) Appl. No.: 10/771,035

(22) Filed: Feb. 3, 2004

(65) Prior Publication Data

US 2004/0157272 A1 Aug. 12, 2004

Related U.S. Application Data

(63) Continuation of application No. 10/093,945, filed on Mar. 9, 2002, now Pat. No. 6,730,492.

(51) Int. Cl.
*C12Q 1/48* (2006.01)
*C12N 9/00* (2006.01)
*C12P 21/06* (2006.01)
*C07K 1/00* (2006.01)

(52) U.S. Cl. .................. 435/15; 435/183; 435/69.1; 530/350

(58) Field of Classification Search .................. 435/15, 435/183, 69.1; 530/350
See application file for complete search history.

(56) References Cited

U.S. PATENT DOCUMENTS

| | | | |
|---|---|---|---|
| 5,625,048 A | 4/1997 | Tsien et al. | |
| 5,928,888 A | 7/1999 | Whitney | |
| 5,958,713 A | 9/1999 | Thastrup et al. | |
| 6,001,619 A | 12/1999 | Beach et al. | |
| 6,048,693 A | 4/2000 | Bitter | |
| 6,093,808 A | 7/2000 | Li | |
| 6,171,780 B1 | 1/2001 | Pham et al. | |
| 6,248,550 B1 | 6/2001 | Tsien et al. | |
| 6,730,492 B1 * | 5/2004 | Cardone et al. | ............ 435/15 |

OTHER PUBLICATIONS

Anandatheerthavarada et al., (1999), "Dual targeting of cytochrome P4502B1 to endoplasmic reticulum and mitochondria involves a novel signal activation by cyclic AMP-dependent phosphorylation at Ser128," *EMBO Journal*, vol. 18, No. 20, pp. 5494-5504.

Burke et al., (1999), "Peptides Corresponding to the N and C Termini of IχB Kinase, IKK-1 and IKK-2," *The Journal of Biological Chemistry*, vol. 274, No. 51, pp. 36146-36152.

DiDonato et al., (1996), "Mapping of the Inducible IχB Phosphorylation Sites that Signal Its Ubiquitination and Degradation," vol. 16, No. 4, pp. 1295-1304.

Li et al., (1999), :Characterization of NFχB Activation by Detection of Green Fluorescent Protein-tagged IχB Degradation in Living Cells, *The Journal of Biological Chemistry*, vol. 274, No. 30, pp. 21244-21250.

Li et al., (1998), "Recombinant IχB Kinases α and β Are Direct Kinases of IχBα," *The Journal of Biological Chemistry*, vol. 273, No. 46, pp. 30736-30741.

Roff et al., (1996), "Role of IχBα Ubiquitination in Signal-induced Activation of NF-χB in Vivo," *The Journal of Biological Chemistry*, vol. 271, No. 13, pp. 7844-7850.

Wacker et al., (1997), "Microtubule-dependent transport of Secretory Vesicles Visualized in real time with a GFP-tagged secretory protein," *Journal of Cell Science*, vol. 110, pp. 1453-1463.

Willems et al., (1999), "SCF ubiquitin protein ligases and phophorylation-dependent proteolysis," *The Royal Society*, vol. 354, pp. 1533-1550.

Winston et al., (1999), "A family of mammalian F-box proteins," *Current Biology*, vol. 9, No. 20, pp. 1180-1182.

Zhang et al., (2001), "Genetically encoded reporters of protein Kinase A activity reveal impact of substrate tethering," *PNAS*, vol. 98, No. 26, pp. 14997-15002.

Zlokarnik et al., (1998), "Quantitation of Transcription and Clonal Selection of Single Living Cells with β-Lactamase as Reporter," *Science*, vol. 279 pp. 84-88.

* cited by examiner

*Primary Examiner*—Maryam Monshipouri
(74) *Attorney, Agent, or Firm*—Goodwin Procter, LLP

(57) ABSTRACT

Cell-based screening methods for determining kinase activity are provided. The methods utilize existing cellular pathways that are regulated by kinases. In one embodiment, various components of a ubiquitin-mediated degradation pathway are modified to create an assay that can be used to screen for a molecule that modulates the activity of a kinase of interest that otherwise does not regulate the degradation pathway. In another embodiment, various components of a protein translocation pathway are modified to screen for a molecule that modulates the activity of a kinase of interest that otherwise does not regulate the translocation pathway.

5 Claims, 8 Drawing Sheets

CELL-BASED SCREENING METHODS

CROSS REFERENCE TO RELATED APPLICATION

This is a continuation of prior application Ser. No. 10/093,945, filed on Mar. 9, 2002, now U.S. Pat. No. 6,730,492, issued May 4, 2004 the entire disclosure of which is incorporated by reference herein.

FIELD OF INVENTION

Methods according to the present invention are generally useful for studying kinase activity in situ and for screening molecules that modulate kinase activities in situ.

BACKGROUND

Optimal drug design largely depends upon drug specificity in the complex context of a living cell. Anti-tumor chemotherapeutic drugs, for example, ideally destroy malignant cells while having a minimal damaging effect on healthy cells. However, most chemotherapeutic drugs have limited specificity and are toxic to both normal and malignant cells. Examples of such side-effects on healthy cells include direct myocardial damage, heart rhythm disturbances, pericarditis, pulmonary fibrosis, hemorrhage, nausea, vomiting, dyspnea, alopecia, peripheral and central neuropathies, pain, nephropathies, stomatitis, diarrhea, fever, immunosuppression, and changes in the state of consciousness. Therefore, cytotoxic side-effects of these chemotherapeutics greatly limit their efficacy.

Many cytostatic drugs, including those used in chemotherapy, function by inducing programmed cell death (apoptosis). However, since many tumor cells arise because of failure to respond to natural cues for apoptosis, they tend to be resistant to chemotherapeutic drugs that aim at triggering apoptotic cues. Therefore, a key strategy of the pharmaceutical industry for treating tumor cell growth is to pre-sensitize cells to apoptotic cues. A means for doing this is to block the protein kinases that inhibit apoptosis, thereby either directly inducing cell death or sensitizing cells to other anti-tumor drugs. Such kinases include the survival kinases AKT, IKK, ERK, Raf-1, PI 3-kinase, PDK-1 and others. Up-regulation of these kinases blocks apoptosis, and is often associated with tumors in humans and other mammals, further suggesting that identification and inhibition of these kinases will be of therapeutic benefit, (e.g., by enhancing the apoptosis-inducing effects of current anti-tumor therapeutics). There is also much interest in finding molecules that inhibit kinases that control other cell functions such as inflammation signaling, cell growth, and cell metabolism. Such inhibitors need to be highly selective in targeting specific kinases in situ.

Presently, most kinase activity measurements are carried out on recombinant proteins, produced and purified from insect cells or from mammalian cells in culture. In vitro assays such as radiometric assays or in-plate binding assays with read-outs are then used to measure the activity of these purified kinases. These in vitro assays are performed under conditions that only marginally reproduce the context of a live cell and are likely to have only marginal biological relevance. Therefore, even when a drug molecule is identified based on its in vitro specificity for a particular kinase, the in situ or in vivo specificity of the molecule remains extremely difficult to assess. Drugs developed using in vitro assays often turn out to have little or no effect in vivo or to have highly toxic side effects such as those mentioned above.

Realizing the importance of examining biological activities inside cells, the pharmaceutical industry is moving towards cell-based screens. However, developing a whole cell screening assay that monitors kinase activity, e.g., in response to an inhibitory molecule, is particularly difficult because of the large number of different kinases within the cell and because of the structural similarities of the catalytic regions of many of these kinases. One approach has been to look at fixed cell imaging of activated kinases. However, this approach only measures whether a kinase has been phosphorylated by an upstream activator kinase. Other approaches rely on a reporting system that is hard to duplicate for multiple kinases, such as the use of fluorescence resonance energy transfer (FRET) technology, which examines an isolated protein-protein interaction that is regulated by a kinase. Because these assays evaluate only a single kinase at a time, they have limited utility for purpose of drug discovery. Further, reporter systems such as FRET are not easily amenable to high-throughput or multiplexing approaches often needed in today's drug discovery programs.

There is, therefore, a need for an in situ kinase assay that determines kinase specificity within a living cell. In particular, an assay is needed that provides information on multiple protein kinases simultaneously, and that provides real-time determination of kinase specificity.

SUMMARY OF INVENTION

The present invention provides kinase assays that are cell-based, and that allow for the discovery of compounds capable of modulating kinase activity in situ. It is an object of the invention to provide methods that can be adapted to assay the activities of different kinases in a cell with relative ease. It is a further object of the invention to provide methods that can screen a candidate molecule, e.g., a small molecule, peptide or drug candidate, regarding its ability to modulate multiple kinases simultaneously. The invention also provides compounds and molecules identified through these methods.

In a preferred embodiment, these and other objects of the invention are accomplished by providing assays based on a cellular signaling event between a signaling enzyme and its substrate. One example of such a signaling event is the binding between the signaling enzyme ubiquitin E3 (E3) ligase, and its substrate. After the binding, the E3 substrate is subject to transubiquitination and targeted by the degradation pathway. Another example of a signaling event on which the invention may be based is part of a peptide translocation pathway. Specifically, the signaling event can be the binding of a transporting protein to a traffic signaling domain of its substrate. After binding takes place, the substrate is eventually transported from a first subcellular area to a second area.

According to the invention, either the signaling enzyme or its substrate is altered so that their interaction is regulated by a kinase of interest. A label is associated with the signaling substrate so that the kinase activity of interest is monitored through the expression of the label as the signaling pathway now targets both the substrate and the label, for example, by degrading or transporting the substrate and the label. Because the signaling pathway takes place in a living cell, monitoring of the kinase activity through the label expression is carried out in situ. When a cell is exposed to a candidate molecule, changes in the expression of the label are indicative of whether the candidate molecule modulates the kinase activity of interest. Because the assay is conducted in live cells, results from the assay provide reliable and relevant information on biological functions and drug specificity.

According to one aspect of the invention, a signaling substrate is altered. In one embodiment, the kinase recognition domain of signaling substrate is modified. For example, an adapter module, e.g., a consensus recognition motif for a kinase of interest, is incorporated into a wild type kinase recognition domain. Alternatively, random mutagenesis can be performed on the wild type kinase recognition domain to produce specificity for the kinase of interest, which can be verified through subsequent screening. Through one or both of the above methods of modification, binding between the altered signaling substrate and the signaling enzyme becomes regulated by the kinase of interest. Using recombinant DNA technologies, an adapter module can be easily incorporated into a peptide. Because the consensus recognition motifs for many kinases are known, methods of the invention generally provide assay systems that can be routinely modified to test large numbers of kinases. These kinases include, but are not limited to, survival kinases implicated in apoptosis, thereby allowing discovery of drugs such as those that can be used in anti-tumor therapies. In an embodiment, a signaling substrate is altered such that its enzyme binding region is flanked by two sequestering motifs that interact with each other. The interaction between the sequestering motifs prevents the signaling substrate from being recognized or bound by the signaling enzyme. The interaction between the sequestering motifs is regulated by a kinase of interest. As a result, binding between the altered signaling substrate and the signaling enzyme is also regulated by the kinase of interest.

In an exemplary method, a candidate molecule is exposed to a cell that expresses a phosphorylation substrate having a kinase recognition domain. The kinase recognition domain is altered to be recognized by a kinase of interest that does not recognize the substrate in its unaltered state. A detectable label is associated with the phosphorylation substrate. This method of the invention further includes determining whether the candidate molecule causes a change in the expression of the label in order to identify a molecule that is capable of modulating the activity of the kinase of interest in situ.

In one embodiment of the invention, the phosphorylation substrate is also the substrate for an E3 ligase. In its unaltered state, binding of the phosphorylation substrate to the E3 ligase is regulated by a wild type kinase, and after the binding takes place, the substrate is eventually degraded by the proteosome. Methods of the invention provide various ways of altering the phosphorylation substrate so that binding between E3 and the substrate, and the ensuing ubiquitin-mediated degradation of the substrate are preserved and regulated by at least one kinase of interest that normally does not regulate the E3 binding event. A label is associated with the substrate, allowing monitoring of E3 binding and providing a readout as a consequence of the cell's exposure to a candidate molecule.

In another embodiment of the invention, the phosphorylation substrate is also the substrate for a transporting protein that causes the substrate to be translocated from a first subcellular area to a second are. In its unaltered state, the phosphorylation substrate's binding with the transporting protein is regulated by a wild type kinase, e.g., through an allosteric modification that affects the structural conformation of the phosphorylation substrate. The modification may change the accessibility by a transporting protein to different traffic signaling regions on the substrate. Binding of the transporting protein to a different signaling region results in translocation of the substrate to a different subcellular area, such as mitochondria, endoplasmic reticulum (ER) or the extracellular space. Methods of the invention provide various ways of altering the phosphorylation substrate such that binding between the transporting protein and the substrate, and the ensuing translocation of the substrate, are preserved and regulated by at least one kinase of interest that normally does not regulate the binding event. A label is similarly associated with the substrate for allowing monitoring the signaling event and any modulation of the signaling event due to cellular exposure to a candidate molecule.

In another embodiment according to the first aspect of the invention, a candidate molecule is exposed to a cell that expresses a signaling substrate whose enzyme binding region is flanked on both sides by two sequestering motifs. When the pair of sequestering motif interact with each other, they prevent the enzyme binding region from binding with the signaling enzyme, for example, because of conformational changes to the substrate. The interaction between the sequestering motifs is regulated by a phosphorylation event that a kinase of interest is responsible for. A detectable label is associated with the signaling substrate and by determining whether the candidate molecule changes the expression of the label in the cell, a molecule capable of modulating the activity of the kinase of interest in situ can be identified. Examples of the signaling substrate include those for an E3 ligase involved in a ubiquitin-mediated degradation pathway, and those for a transporting protein involved in a peptide translocation pathway.

According to another aspect of the invention, the signaling enzyme is altered. In one embodiment, an adapter module, whose ability to recognize and bind to its ligand is regulated by a kinase of interest, is incorporated into the signaling enzyme. Through the adapter module, the altered signaling enzyme becomes capable of recognizing and binding the ligand of the adapter module, subject to regulation by the kinase of interest. In another embodiment, random mutagenesis is performed on a portion of the signaling enzyme, preferably the substrate-binding portion, so that the mutant enzyme recognizes and binds a phosphorylation substrate having a particular phosphorylation state.

In one embodiment, a candidate molecule is exposed to a cell that expresses a signaling enzyme that is altered to bind a phosphorylation substrate for a kinase of interest that, in its unaltered state, the signaling enzyme does not bind. A detectable label is associated with the phosphorylation substrate. Further, binding between the altered signaling enzyme and the substrate is regulated by a kinase. This method of the invention further includes determining whether the candidate molecule causes a change in the expression of the label in order to identify a molecule that is capable of modulating the kinase activity in situ. Examples of the signaling enzyme include an E3 ligase involved in a ubiquitin-mediated degradation pathway, and a transporting protein involved in a peptide translocation pathway.

According to another aspect of the invention, assays according to any of the above-described embodiments of the invention are multiplexed to study multiple kinases by using differentiable labels that are each associated with a different kinase substrate. For example, multiple phosphorylation substrates may each be mutated to contain a kinase recognition domain for a different kinase, each substrate associated with a differentiable label. Examples of such labels include GFP and its variants, which fluoresce at differentiable wavelengths. Expressing these multiple kinase substrates in one of the cell-based assay systems described above allows monitoring of kinase regulation of a signaling event and any modulation thereof by a candidate molecule to which the cell is exposed. An application of the multiplexed embodiment is the screening for a molecule for specificity for multiple kinases in the same signaling pathway.

The invention also provides molecules identified through one of the methods described wherein the molecule is capable of modulating a kinase activity in situ. The invention also provides fusion proteins useful for the methods described, isolated genetic molecules encoding the fusion proteins, vectors capable of expressing the genetic molecules, and cells transfected with at least one of such vectors.

DETAILED DESCRIPTION

Cellular signaling pathways include signaling events in which a signaling enzyme interacts with a substrate and subsequently causes the substrate to be targeted by the rest of the signaling pathway. Some signaling events are regulated by a kinase: some require phosphorylation of a substrate at a specific amino acid position by a wild type kinase; some require non-phosphorylation or dephosphorylation of a substrate at a specific amino acid position. Others signaling events do not depend on any phosphorylation event. For example, binding between a ubiquitin E3 ligase (E3 ligase)—a signaling enzyme—and its substrate can fall under any of these categories. In some cases, E3 ligase binding is regulated by a kinase, and in other cases it is not. E3 ligase recognition and binding to a substrate causes the substrate to be targeted by the ubiquitin-mediated degradation pathway. Other examples of signaling events include, but are not limited to, binding of a transporting protein—a signaling enzyme—to the traffic signaling domain of its substrate, which then causes the substrate to be targeted by a protein translocation pathway.

I. Altered Signaling Substrate

In one aspect of the invention, methods are provided for a cell-based screening method by altering the substrate for a signaling enzyme (a "signaling substrate") that is implicated in a cellular signaling pathway.

(a) Altered Kinase Recognition Domain

Figure 1:
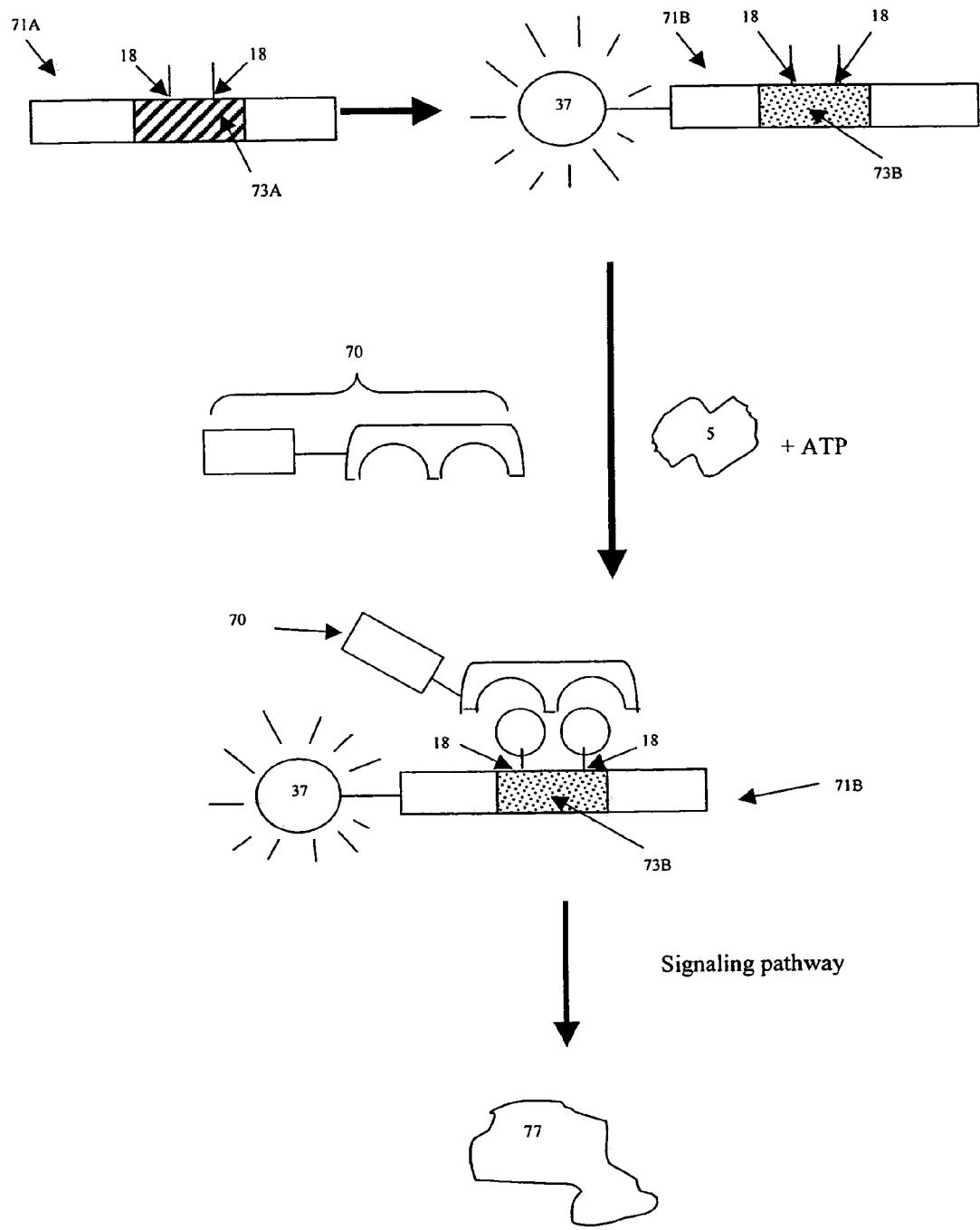
FIG. 1 illustrates an embodiment of the invention.

Referring to FIG. 1, in one embodiment, a signaling event, in its unaltered state, is normally regulated by a particular kinase (e.g., its wild type kinase). In other words, binding between a signaling enzyme 70 and its wild type substrate 71A normally depends on the phosphorylation state of one or more key amino acid residues 18 in the substrate 71A. The wild type kinase recognition domain 73A of the wild type signaling substrate 71A may be modified (e.g., through genetic mutation) to create an altered signaling substrate 71B. For example, an adapter module such as a consensus recognition motif for a kinase of interest 5, can be incorporated into the wild type kinase recognition domain 73A to create an altered kinase recognition domain 73B. Alternatively, random mutagenesis can be performed on the wild type kinase recognition domain 73A to introduce specificity for the kinase of interest 5. In a preferred embodiment, the key amino acid residues 18 are not disrupted by the modification in the wild type kinase recognition domain 73A.

Under suitable conditions (e.g., activation of the kinase of interest 5), the altered signaling substrate 71B may be phosphorylated by the kinase of interest 5 at, e.g., the key amino acid residues 18. If the recognition and binding by the signaling enzyme 70 requires phosphorylation of the signaling substrate 71A, then, when the altered signaling substrate 71B is phosphorylated by the kinase of interest 5, the signaling pathway will target the altered substrate 71B and produce a signaling product 77. Conversely, if the recognition and binding by the signaling enzyme 70 requires non-phosphorylation of the signaling substrate 71, then, when phosphorylation of the altered signaling substrate 71B by the kinase of interest 5 is inhibited, the signaling pathway will target the altered substrate 71B and produce the signaling product 77. As a result, the signaling event is altered or converted to be regulated by the kinase of interest 5.

In an embodiment, a candidate molecule may be exposed to a cell where the converted signaling event takes place. The candidate molecule can be either a macromolecule such as a protein, a small molecule, or a drug candidate, for example. If the candidate molecule changes (e.g., stimulates or inhibits) the altered signaling event, it is indicative that the molecule may be capable of modulating the activity of the kinase of interest 5 in vivo. Therefore, by altering kinase specificity for its substrate, an in situ signaling event with a characterized readout can be modified many times to screen for drug candidates against many different kinases of interest 5. Because methods of the invention are conducted in living cells, results are specific and biologically relevant.

Still referring to FIG. 1, to monitor or provide readout for the altered signaling event, a detectable label 37 is associated with the altered signaling substrate 71B which participates in the altered signaling event so that the label 37 is expressed as a result of activation of the altered signaling pathway. The label 37 provides a detectable signal that has a distinguishable physical or chemical property, including, but not limited to, fluorescence, radioactivity, color, sound, heat, or changes thereof. The label 37 may be associated with the altered signaling substrate 71B through various means including, but not limited to, conjugation, fusion, linkage, or enzymatic interaction. For example, the label 37 may be the enzymatic substrate targeted by a product from the signaling pathway. Expression of the label 37 can be determined as a change in its signal, e.g., increase or decrease in the signal intensity, duration or location. An example of such expression is the destabilization or degradation of a fluorescent label associated with a substrate, which causes a decrease or disappearance of fluorescence. The label 37 can be used to monitor the occurrence of the altered signaling event, and when the signaling event is regulated by a kinase of interest 5, the label can be used as an indicia of the activity of the kinase of interest 5.

(b) Ubiquitin-Mediated Degradation

In an embodiment, methods of the invention can exploit certain ubiquitin-mediated degradation pathways to provide a reporter system for kinase function. In certain cases, a signaling event in this pathway, the binding between an E3 ubiquitin ligase (E3 ligase) and its substrate, is normally regulated by a wild type kinase. Therefore, it is possible to alter this binding event in order to study the activities of other kinases and to screen for molecules that modulate such activities in situ.

Ubiquitin-mediated degradation of proteins is a means by which a cell controls the abundance of proteins, especially signaling proteins such as enzymes, thereby controlling various signaling pathways. For example, in the regulation of the cyclin dependent kinases (CDK), ubiquitins are covalently attached to the CDK in a process called "transubiquitination," thereby targeting the CDK for degradation by the 26S proteosome. See DM Koepp, et al., *Cell,* 97(4): 431–34 (1999). The machinery for ubiquitination is fairly well characterized and includes the ubiquitin activating enzyme (E1), the ubiquitin conjugating enzyme (E2), and ubiquitin ligase (E3 ligase). E3 ligase is responsible for substrate recognition and confers high specificity to the transubiquitination process. In certain cases, the E3 ligase functions in a phosphorylation-dependent fashion. For example, one class of E3 ligases called the SKP1-Cdc53/Cullin-F-box protein (SCF or F-box protein) ubiquitin ligase recognizes and binds to its substrate only when the substrate is phosphorylated at a certain serine/threonine site. See J T Winston et al., *Curr Biol.* 9(20): 1180–82 (1999).

Figure 2A:
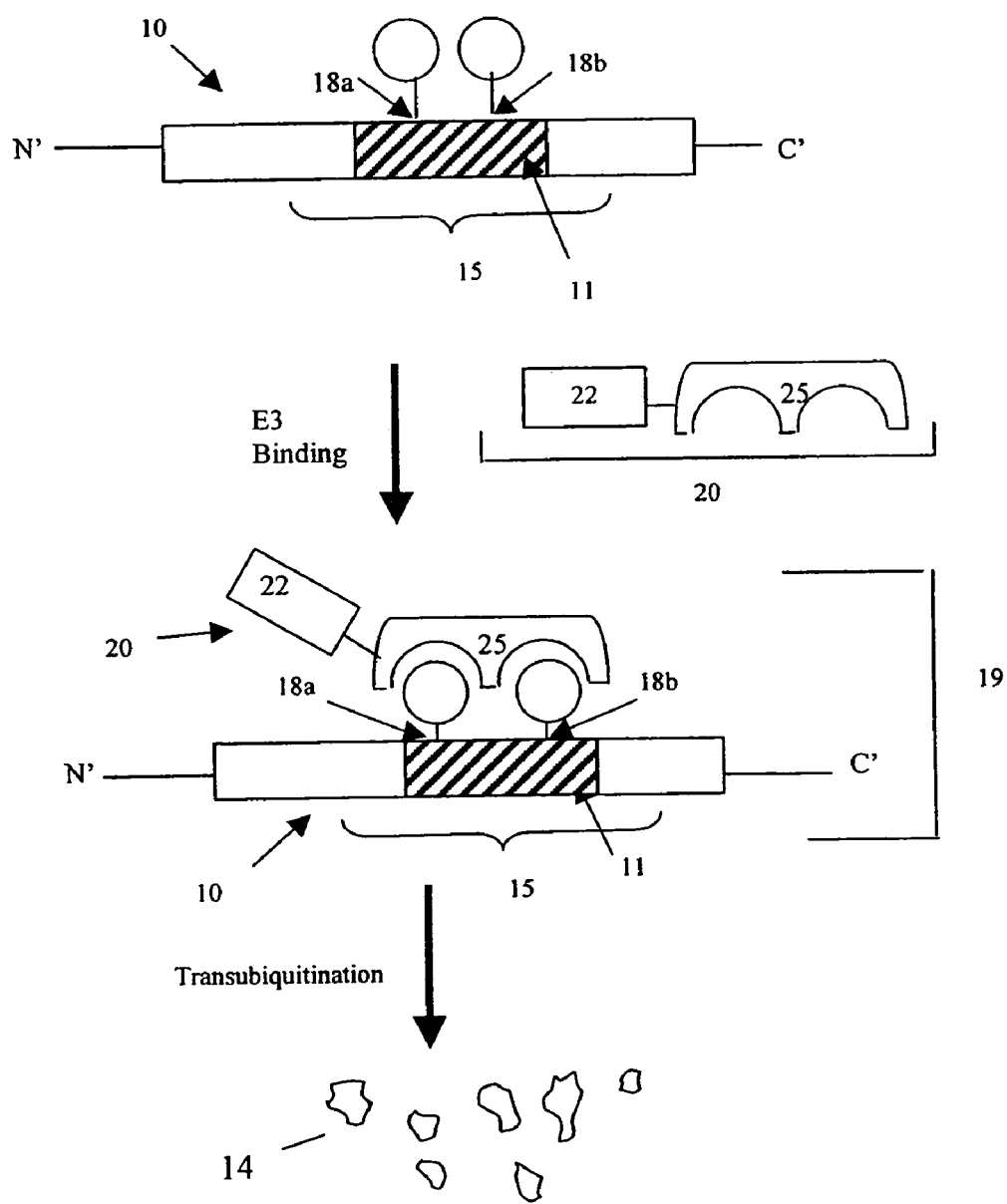
FIG. 2A illustrates a wild type kinase-regulated and ubiquitin-mediated protein degradation pathway.

Referring to FIG. 2A, an unaltered (i.e., wild type) E3 substrate 10 contains an E3 binding region 11 and a wild type kinase recognition domain 15. The E3 binding region 11 and the kinase recognition domain 15 may overlap or may be two disparate parts of the E3 substrate 10; their relative positions are not limited to the configuration illustrated in FIG. 2A. Overlap between the two includes the situation where one is entirely within the other.

When one or more amino acid residues, for example, 18a and 18b, in the kinase recognition domain 15 become phosphorylated by at least one wild type kinase 40, an E3 ligase 20 is able to recognize and bind the wild type E3 substrate 10 at the E3 binding region 11 and forms an E3 ligase-E3 substrate complex 19 with the E3 substrate 10. The E3 ligase 20 includes an N-terminus 22 and a C-terminus 25. In an embodiment, binding of the E3 ligase 20 to the substrate 10 occurs through the C-terminus 25. The E3 ligase-E3 substrate complex 19 further complexes with the E2 and E1 proteins (not shown) and eventually causes the transubiquitination and degradation of the wild type substrate 10 into degradation product 14.

Figure 2B:
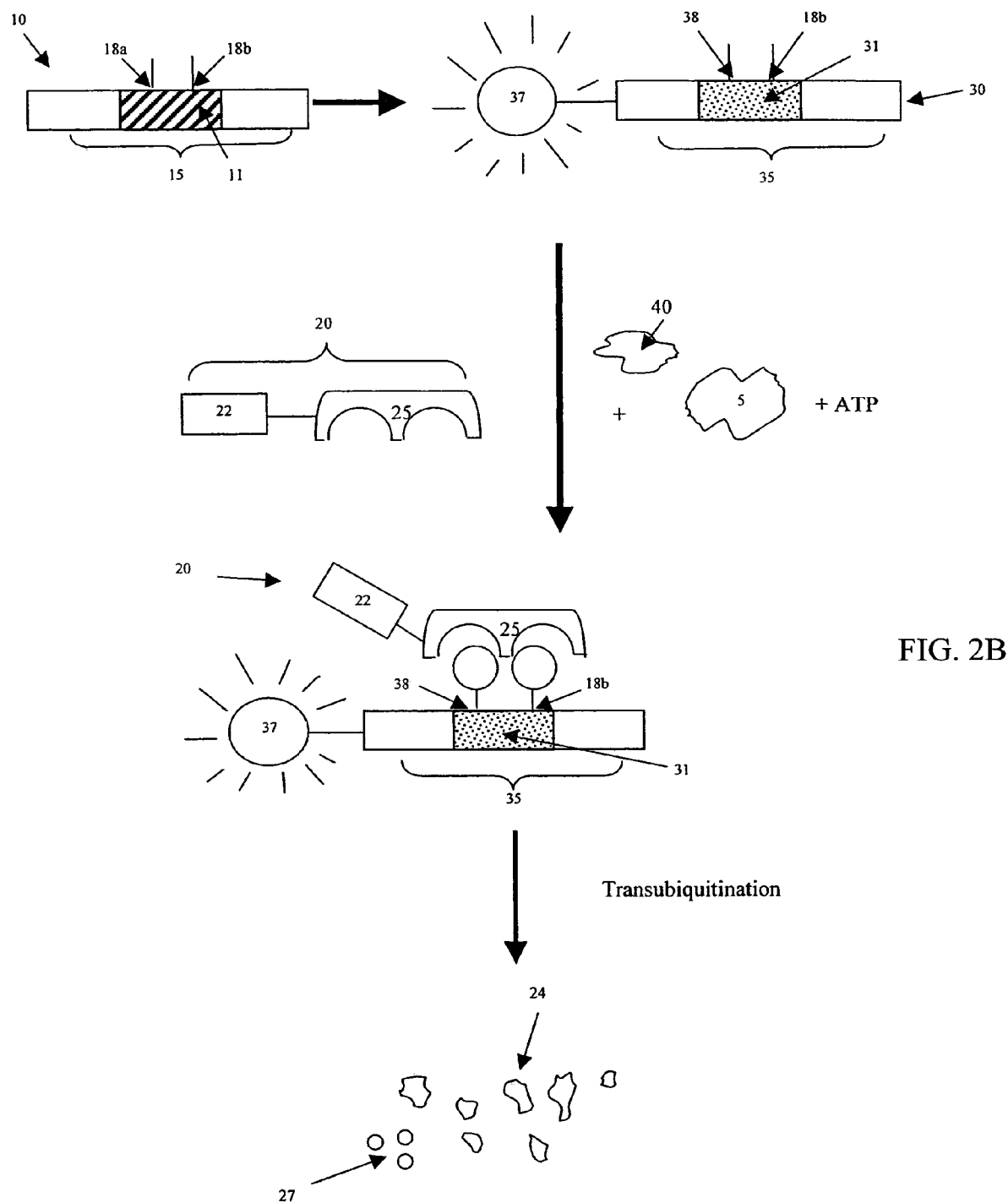
FIG. 2B illustrates one embodiment of the invention utilizing a reengineered ubiquitin-mediated protein degradation pathway.

In an embodiment according to the invention, the kinase specificity of the ubiquitin-mediated degradation pathway may be altered by modifying the wild type E3 substrate. Referring to FIG. 2B, a wild type E3 substrate 10 includes a wild type kinase recognition domain 15 where one or more key amino acid residues, for example, 18a and 18b are phosphorylated by at least one wild type kinase 40. The wild type kinase recognition domain 15 is altered by genetic mutation so that it is recognized by a kinase of interest 5, resulting in an altered E3 substrate 30 having an altered kinase recognition domain 35. Genetic mutation includes insertion, deletion or substitution of one or more amino acid residues and may be accomplished through mutating the nucleic acid sequence, e.g., DNA, that encodes the wild type kinase recognition domain 15. In one embodiment, the wild type recognition domain 15 is mutated to contain a consensus kinase recognition motif known to be specific for a kinase of interest 5. The consensus recognition motif functions as an adapter module that converts the wild type E3 substrate 10 into an altered E3 substrate 30, which is specific for, e.g., binding to a the kinase of interest 5. The alteration or mutation of the wild type E3 substrate 10 should be designed so as to not substantially affect phosphorylation-regulated E3 binding. In one embodiment, a key amino acid 18a, in the wild type kinase recognition domain 15, is mutated to a replacement amino acid 38 in the altered kinase recognition domain 35, and phosphorylation of the altered E3 substrate 30 takes place at residue 38. In another embodiment, a change in amino acid sequence in the wild type E3 substrate 10 occurs outside the wild type E3 binding region 11. In that case, altered E3 binding region 31 has the same amino acid sequence as the wild type E3 binding region 11.

For example, the portion of the wild type kinase recognition domain 15 upstream or including the key amino acid residue 18a may be mutated such that replacement amino acid residue 38 is recognized and phosphorylated only by a kinase of interest 5, but no longer the wild type kinase 40. The other key amino acid residue 18b may remain recognized and phosphorylated by the wild type kinase 40, resulting in an altered E3 binding event regulated by two kinases.

Still referring to FIG. 2B, the altered E3 substrate 30 is further associated with a label 37. The label 37 may be associated with the altered E3 substrate 30 through any method known to a skilled artisan. For example, the label 37 may be expressed as part of a fusion protein that includes the altered E3 substrate 30, as shown specifically in FIG. 2B. Or, the label 37 may be associated with the altered E3 substrate 30 through protein conjugation, or is not directly linked to the altered E3 substrate 30 (e.g., the label 37 may be an enzymatic product which participates down stream of the altered E3 substrate 30 phosphorylation event). The position of the label 37 in relation to the altered E3 substrate 30 is not limited to that shown in FIG. 2B, as long as the label 37 does not disrupt the function of the E3 substrate 30.

The label 37 used in these experiments and for other embodiments of the invention should be able to produce a detectable signal, such as a fluorescent signal or a detectable enzymatic product. In one embodiment, the label 37 is a fluorescent protein, which includes any protein capable of fluorescing when excited with appropriate electromagnetic radiation, whether the protein's amino acid sequence is natural or engineered. An example of a fluorescent protein is a green fluorescent protein (GFP), such as a wild type GFP from the jellyfish *Aequorea Victoria*, which generates green fluorescence when excited by light at the wavelength around 498 nM. GFP gives strong fluorescence once expressed in a cell, and the transfected cell can be easily detected and analyzed using a combination of fluorescence microscopy and image analysis. GFP is a preferred label at least in part because it gives a real time readout. Other variants of GFP, such as those with modifications that change the spectral properties of the GPF fluorescence including CFP and YFP or other fluorescent molecules, are also contemplated by the invention.

In another embodiment, the label 37 is an enzyme that is able to produce a signal by generating a detectable enzymatic product. "Enzymatic product" is intended to include products and by-products of an enzymatic reaction, such as radiation, changes in color, and other physical or chemical changes. Example of such enzymatic labels include beta-galactosidase, firefly luciferase, secreted alkaline phosphatase, chloramphenicol acetyl transferase, and β-lactamase. For example, U.S. Pat. No. 5,928,888 to Whitney, describes using β-lactamase as a reporting label.

Still referring to FIG. 2B, binding between the E3 ligase 20, which includes N-terminus 22 and C-terminus 25, and the altered E3 substrate 30 depends on whether the amino acid at position 38 is phosphorylated or not phosphorylated by the kinase of interest 5. FIG. 2B depicts an embodiment of the invention in which phosphorylation at position 38 is required for E3 ligase 20 binding. In this embodiment, when the amino acid at position 38 is phosphorylated by the kinase of interest 5, E3 binding to the altered E3 binding region 31 takes place. This causes the altered E3 substrate 30 and its associated label 37 to undergo transubiquitination and to produce degradation product 24 and 27 respectively. As a result, the signal from the label 37 decreases or disappears.

In an embodiment, a cell is transfected to express the altered E3 substrate 30 fused to the label 37. The altered E3 substrate 30 contains an altered E3 binding region 31, an altered kinase recognition domain 35 specific for a kinase of interest 5, and a label 37. When the kinase of interest 5 is expressed and activated in the cell (e.g., endogenously or exogenously), the kinase of interest 5 is able to regulate the phosphorylation state of the altered E3 substrate 30 at position 38. As a result, the kinase of interest 5 is able to regulate the binding between the E3 ligase 20 and the altered E3 substrate 30. If E3 binding takes place, the altered E3 substrate 30 and its associated label 37 are targeted by the ubiquitin degradation pathway, which eventually results in an expression of the label 37 through a loss of signal.

To screen for a candidate molecule capable of modulating an activity of the kinase of interest 5, the transfected cell is exposed to a candidate molecule (not shown). For example, if binding of the E3 ligase 20 to the altered E3 substrate 30 requires phosphorylation at amino acid position 38 by the kinase of interest 5, and the candidate molecule has an inhibitory effect on the activity of the kinase of interest 5, the modified E3 substrate 30 is stabilized and disappearance of the label 37 due to phosphorylation is inhibited. In other words, if the label 37 remains detectably stable after the cell is exposed to a candidate molecule, it is indicative that the candidate molecule may have an inhibitory effect on the activity of the kinase of interest 5. Conversely, if the candidate molecule has a stimulatory effect on the kinase activity, the modified E3 substrate 30 is further destabilized and disappearance of the label 37 due to phosphorylation is detectably enhanced. Thus, by quantifying the amount of the label 37, by methods known in the art, the modulating effect of the candidate molecule can be determined and/or quantified.

It is also possible that the observed modulatory effect of a candidate molecule on a signaling event such as the degradation of the altered E3 substrate 30 results from interactions other than those that affect the kinase function. Routine control experiments can be used to eliminate the possibilities in order to evaluate specific modulatory effect on the kinase function. For example, if an overall inhibitory effect is observed, there can be other explanations besides the inhibition of the activity of the kinase of interest 5. Those other explanations may include the inhibition of the activity of the wild type kinase 40 if it still participate in the regulation of the binding between the E3 ligase 20 and the altered E3 substrate 30, inhibition of the 26S proteosome, or inhibition of binding between the E3 ligase 20 and the phosphorylated altered E3 substrate 30. Control experiments useful in evaluating these possibilities may include expressing, in a cell, substrates of multiple E3 ligases, including the wild type version of altered E3 substrate 30 (i.e., E3 substrate 10), each fused to a discreet label, in the presence of the inhibitor molecule. By determining which of these substrates is destabilized, it can be determined whether the inhibitory effect likely results from inhibiting the activity of the kinase of interest 5.

To illustrate, if proteosome function is inhibited, all of the E3 substrates should be stabilized and their respective label should be detectable. If both the wild type E3 substrate 10 and the altered E3 substrate 30 are stabilized, but other E3 substrates are not, it is likely that the activity of wild type kinase 40, which is required for the degradation of both substrates 10 and 30 in this example, is inhibited by the drug candidate molecule. When only the altered E3 substrate 30 is stabilized, and all the other substrates including wild type E3 substrate 10 are destabilized, it is likely that the drug candidate molecule specifically inhibits the kinase of interest 5.

The kinase of interest 5 may be any kinase and may include those that are not recognized by the E3 substrate in its unaltered state. It may also include a wild type kinase 40 in some cases. The recognition sequence for the kinase of interest 5 may be known or unknown when it comes to genetically modifying the wild type kinase recognition domain 15 into the altered kinase recognition domain 35 specific for a kinase of interest 5. If the recognition sequence for the kinase of interest 5 is not known, the wild type kinase recognition domain 15 may be randomly mutated to screen for the recognition sequence specific for a given kinase of interest 5. In an exemplary method, an altered E3 substrate 30 with a randomly mutated kinase recognition domain 35 and fused to the label 37, is expressed in a live cell. The cell is then treated with an inhibitor of the wild type kinase 40, while activating the kinase of interest 5, in order to screen for the optimal sequence that would make the altered E3 substrate 30 recognized and phosphosphorylated by the kinase of interest 5 without substantially compromising phospho-dependent E3 ligase binding. For example, if phosphorylation of the E3 substrate is required for E3 binding, the desired mutation can be identified when the label 37, e.g., fluorescent or enzymatic, is destabilized, suggesting that binding between the kinase of interest 5 and the altered recognition domain 35 leading to the degradation of the altered substrate 30 and the label 37. As a negative control, a non-phosphorylated form of the same altered E3 substrate (e.g., by inhibiting the kinase of interest 5), may be provided to test the same altered sequence. The screen may be routinely performed on a high-density multiplexed protein array where individual clones of cells transfected with a copy of the mutated E3 substrate 30 is arrayed.

When the recognition sequence, e.g., a consensus motif, for the kinase of interest 5 is known, it is possible to design and create site-specific mutation to incorporate that sequence into the wild type E3 substrate 10 to create the altered E3 substrate 30. Additionally, through random substitutions of amino acid residues that surround the consensus motif in the altered kinase recognition region 35, its specificity for phospho-dependent binding with the E3 ligase 20 may be enhanced. See MB Yaffe et al., *Methods Enzymol.* 328: 157–70 (2000). For example, nucleic acid constructs expressing randomly mutated amino acid residues surrounding a consensus motif may be shotgun transfected into tester cell lines. Pooled clones may then be evaluated for successful conversion or alteration of the wild type E3 susbstrate 10, again with the readout being kinase-regulated stability of the altered E3 substrate 30 and the associated label 37. The kinase of interest 5 may be activated with known activating molecules or expressed in the screening cell line as a constitutively active kinase.

An exemplary signaling enzyme whose function can be used to practice the invention is Beta-TrCP, an E3 ligase. For example, Beta-TrCP recognizes the NFkB-regulating protein IκB-α after IκB-α has been phosphorylated by the cytokine inducible IκB kinase (IKK). The ubiquitination of IκB-α specifically depends upon its phosphorylation at residues serine 32 or serine 36 in exon 1. Mutating these serines to alanines blocks transubiquitination. See M. Roffet al., *J Biol Chem.,* 271(13): 7844–50 (1996). Other phosphorylation-dependent substrates of beta-TrCP include the transcription factor Beta catenin, requiring prior phosphorylation by GSK3B at serines 33 and 37, and the HIV protein VPU, which requires phosphorylation at serine 52 and 56 by casein kinase 2 (CK2). In each of these wild type substrates for Beta-TrCP, two phosphorylated residues, which can be either serine or threonine (S/T) at both positions, are found within the Beta-TrCP binding region 11 containing the sequence D(S/T)GXX(S/T), where X represents any amino acid.

Referring to FIG. 2B, in an exemplary method of the invention, a wild type E3 substrate IκB-α 10 is converted from being regulated by a wild type kinase IKK 40 to being regulated by AKT, a kinase of interest 5, by mutating the wild type E3 substrate IκB-α 10. Referring now to FIG. 3A, the IKK recognition domain on the wild type IκB-α is presumably within LD (27) DRH<u>DS(32)GLDS(36)</u> MKDE found in the first exon of IκB-α, where the underlined residues constitute the Beta-TrCP binding region 11 of D(S/T)GXX(S/T). Here, the wild type Beta-TrCP binding region 11 overlaps with the wild type kinase recognition domain 15 in the sense that region 11 is entirely within the domain. Phosphorylation of both residues at positions 32 and 36 (two serines in the wild type case) are required to cause targeting of IκB-α to the proteosome for transubiquitination.

Still referring to FIG. 3A, according to one embodiment of the invention, the wild type IKK recognition domain of E3 substrate IκB-α may be converted into the altered kinase recognition domain 35 that is recognized and phosphorylated by IKK. The consensus recognition motif for AKT, the kinase of interest 5, is known to be RXRXX(S/T), where X is any amino acid and where the serine (S) or threonine (T) is phosphorylated by AKT. AKT recognition motif may be introduced into IκB-α 10 by mutating the aspartic acid (D) at position 27 to an arginine (R) and mutating the serine (S) at position 32 to a theonine (T), resulting in a converted sequence of L<u>R(27)DRHDT(32)</u> GLDS (36) MKDE in the altered E3 substrate 30. The underlined residues constitute the converted domain 35 for AKT recognition where T (32) is phosphorylated by AKT.

The change of S(32) to T(32), while having little impact on AKT phosphorylation, limits the residue that can be efficiently phosphorylated by IKK in situ to S(36). See J DiDonato et al. *Mol. And Cell. Biology,* 16 (4), 1295–04 (1996); and J Li et al. *J. of Biological Chem.* Vol. 273, No.46, 30736–41 1998). The inability of IKK to efficiently phosphorylate threonine in place of serine at position 32 offers the opportunity to convert transubiquination's requirement for IKK phosphorylation to a dual kinase requirement. The additional non-wild type kinase is preferably a serine/threonine kinase such as AKT.

Referring still to FIG. 3A, the replacements of D(27) with R(27) is outside of the wild type Beta-TrCP binding region 11, and therefore the mutation is unlikely to disrupt the binding of Beta-TrCP. The replacement of S(32) with T(32) results in an altered Beta-TrCP binding region 31 with a sequence, as boxed in FIG. 3, of DTGLDS, substantially similar to the wild type Beta-TrCP binding region 11 (also boxed), and conforms with the conserved Beta-TrCP binding sequence D(S/T)GXX(S/T) described above. Therefore, mutations in IκB-α at positions 27 and 32 both have only minimal effect, if any, on the altered IκB-α 30's ability to bind with Beta-TrCP. However, for Beta-TrCP to recognize and target the altered IκB-α substrate 30 to the degradation pathway, phosphorylation by both AKT and IKK is now required.

Optionally, the requirement for IKK phosphorylation can be completely eliminated. For example, the S (36) in the converted sequence of the altered E3 substrate 30 shown in FIG. 3A may be replaced by a phosphomimetic amino acid residue, either an aspartic acid or glutamic acid. The resulting converted sequence is L<u>R(27)DRHDT(32)</u> GLD(D/E) (36) MKDE. The replacement residue mimics the phosphorylated serine at position 36. See Lin R. et al. *Mol Cell Biol.* 8(5):2986–96 (1998). As a result, activation, i.e., Beta-TrCP binding, of the altered IκB-α 30 is solely AKT dependent.

Since the altered kinase recognition domain 35 is situated in the first exon of IκB-α, a label 37, e.g., a GFP, may be fused 5' of the first exon of the altered IκB-α 30. The sequence to which the label 37 is fused may consist, for example, of residues 1–320 of IκB-α (Genbank accession number P25063) with mutation at positions 27 and 32 as described. Other options for associating a GFP to IκB-α can be found in, for example, U.S. Pat. No. 6,093,808.

In an embodiment, mammalian expression vectors coding for the altered E3 substrate 30 and its label 37 may be introduced into a cell (e.g., a cell line such as human Jurkat cell line which responds to both TNFα and insulin). Cells are treated with various combinations of activators and inhibitors of either IKK or AKT to ensure that activation of both kinases is required for non-detection of the label 37 as a result of ubiquitin-mediated degradation. For example, IKK activators include tumor necrosis factor alpha (TNFα), which is activated through the TNF receptor, and phorbol myristate acate (PMA). Inhibitors of the IKKs include the E1A oncogene and several poly phenols. See R. Shao et al. *J Biol Chem.* 30;274 (31):21495–8 (1998) and F. Yang et al.,

*Mol Pharmacol.* 60(3):528–33 (2001). AKT activators include insulin, and AKT inhibitors include wortmanin. In a preferred embodiment where the label 37 is wild type GFP, the signal from the GFP 508 nM, may be monitored using a 96 well plate fluorimeter. Candidate molecule libraries may be screened in these transfected cell lines in order to identify compounds that alter AKT and/or IKK activity, as described above.

Methods of the invention are not limited to any particular kinase. For example, recognition motifs for kinases other than those described above may be engineered into IκB-α's kinase recognition domain 15 to change its specificity for other kinases. For example, the consensus recognition motif for a p34cdc2 kinase is X(S/T)PXR wherein the amino acid to be phosphorylated can be either S or T. Again starting with the IKK-recognition domain 15 on IκB-α which has the sequence LDDRHDS(32)GLDS(36) M(37)KD(39)E, the underlined portion being the E3 binding region 11. If residue S(36) is mutated into T(36), M(37) into P(37), and D(39) into R(39), the sequence will be altered to LDDRHDS (32) GLDT(36)P(37)KR(39)E, wherein the underlined portion represents the consensus recognition sequence for p34cdc2, which phosphorylates T(36). In addition to T(36), S(32) needs to be phosphrylated by IKK to be recognized by Beta-TrCP, an E3 ligase. The change of S(36) to T(36), plus IKK's inability to efficiently phosphorylate T(36), changes transubiqutination's original requirement for IKK phosphorylation to a dual phosphorylation requirement for IKK and p34cdc2 kinase. Optionally, S(32) may additionally be replaced by a phosphomimetic residue, either D or E. As described in an earlier embodiment, because D or E mimics the phosphorylated S, Beta-TrCP binding becomes solely regulated by p34cdc2 kinase and not IKK.

Besides IκB-α, other wild type E3 substrates such as Beta catenin, HIV protein VPU, p27, Bcl-2, and c-Jun may also be altered into an altered E3 substrate 30 where altered kinase recognition domain 35 for a kinase of interest 5 is introduced. In the case of mammalian p27, after it is phosphorylated by cyclin E cdk-2, a mammalian E3 ligase Skp2 targets it to the ubiquitin-mediated degradation pathway. The cdk-2-specific kinase recognition domain 15 may be mutated to contain the altered kinase recognition domain 35 for a kinase of interest 5.

Figure 3A:
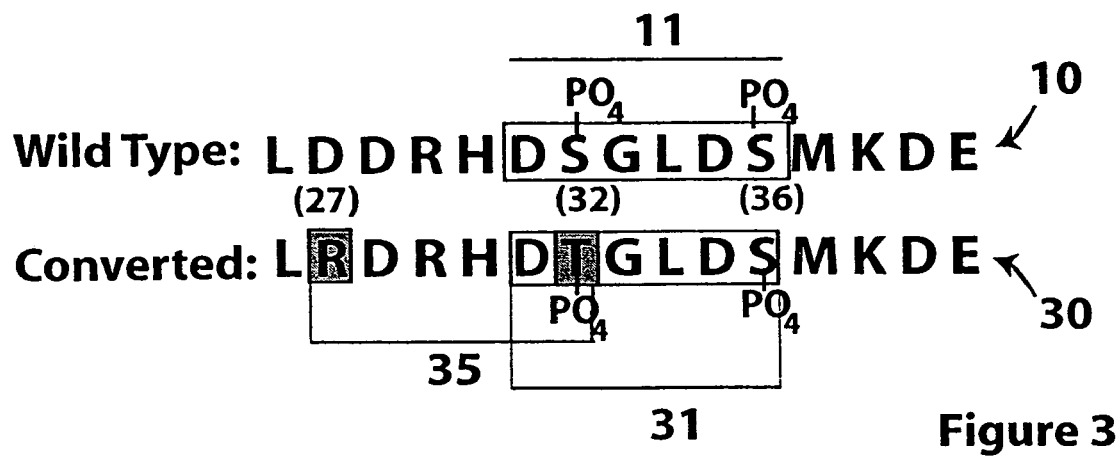
FIG. 3A illustrates a strategy for modifying a region of IκB-α such that it contains an AKT consensus recognition motif.
Figure 3B:
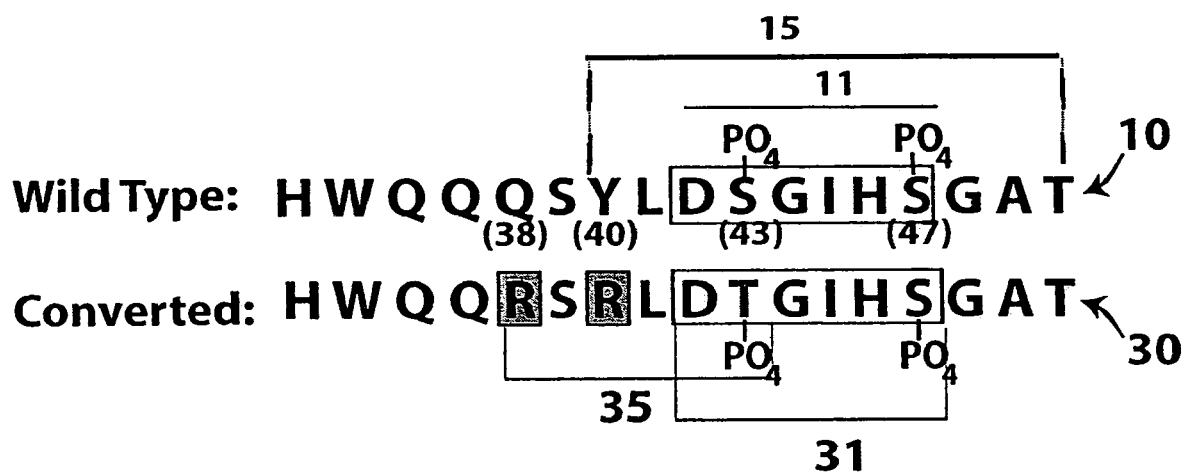
FIG. 3B illustrates a strategy for modifying a region of Beta catenin such that it contains an AKT consensus recognition motif.

Referring to FIG. 3B, for example, in Beta catenin, the wild type kinase recognition domain 15 is Y(40)L DS(43)GIHS(47)GAT, where S (43) and S(47) are both phosphorylated by the kinase GSK3B. To incorporate an AKT recognition site (RXRXX(S/T)), for example, both residues Q(38), which is outside the kinase recognition domain 15, and Y(40) may be mutated into R(38) and R(40) respectively, and S(43) may be mutated into T(43), converting the sequence into the altered kinase recognition domain 35: R(38)S(39)R(40)LDT(43). The mutated substrate 30 requires phosphorylation at S(47) by GSK3B and phosphorylation at T(43) by AKT for E3 recognition and binding to take place. Again, to eliminate GSK3B requirement, the S(47) in the converted sequence may additionally be replaced by a phophomimetic residue, either D or E. As described in earlier embodiments, because D or E mimics the phosphorylated S, E3 binding only requires phosphorylation by AKT at (S/T)(43). Note that serine (43) does not have to be replaced by T in this alternative embodiment.

In the case of Bcl-2, E3 binding is normally regulated by wild type kinases ERK 1 and ERK 2-phosphorylation of Bcl-2 at a certain serine and threonine by ERK 1 and ERK 2 prevents E3 binding and inhibits degradation of Bcl-2. In a particular embodiment of the invention, Bcl-2 is mutated around the designated serine/threonine, such as the T(74) and S(87) shown in Table 1 below, to contain a recognition domain for a kinase of interest that normally does not recognize Bcl-2. Table 1 lists possible mutations around the phosphorylation sites so that the sequences around them become recognition domains for kinases of interest such as CHK 1, CHK2, or AKT, respectively. The underlined residues in the wild type Bcl-2 kinase recognition domain can be mutated to the residues shown for each kinase of interest while the other amino acid residues remain the same, including the amino acid residues to be phosphorylated, i.e., T(74) and S(87). As a result, ubiquitin-mediated degradation of the altered Bcl-2 becomes regulated by these kinase of interest respectively, instead of by ERK1 or ERK 2. When the altered Bcl-2 is associated with a detectable label, regulation of the degradation of the altered Bcl-2 by the kinase of interest or modulation of such regulation by a candidate molecule can be monitored by determining expression levels of the label.

TABLE 1

Altered Bcl-2 Sequence

| | | | | |
|---|---|---|---|---|
| Wild type Bcl-2 (ERK1/2 substrate) | R<u>TS</u>P<u>L</u>QT(74)<u>PA</u> | | A<u>AG</u>P<u>A</u>LS(87)<u>PVP</u> | |
| Altered Bcl-2 (CHK1/2 substrate) | L R | F | L R | F |
| Altered Bcl-2 (AKT substrate) | R R | | R R | |

In the case of c-Jun, E3 binding is normally regulated by the wild type kinase JNK 1 through phosphorylation at certain serines. In a particular embodiment of the invention, c-Jun is mutated around serines, for example, the S(63) and S(73) shown in Table 2 below, to contain a kinase recognition domain for a kinase of interest that normally does not recognize or phosphorylate c-Jun. Table 2 lists possible mutations around the phosphorylation sites that create kinase recognition domains for kinases of interest such as CHK 1, CHK2 or AKT respectively. The underlined amino acid residues in the wild type c-Jun kinase recognition domain can be mutated to the residues shown for each kinase of interest while the other residues remain the same, including the residues to be phosphorylated, i.e., S(63) and S(73). As a result, ubiquitin-mediated degradation of the altered c-Jun becomes regulated by these kinases of interest respectively, instead of by JNK1. When the altered c-Jun is associated with a label, regulation of the degradation of the altered Bcl-2 by the kinase of interest or modulation of such regulation by a candidate molecule can be monitored through expression of the label.

TABLE 2

Altered c-Jun Sequence

| | | | | |
|---|---|---|---|---|
| Wild type Bcl-2 (JNK1 substrate) | <u>SDL</u>LTS(63)<u>PDV</u> | | G<u>LLK</u>LAS(73)<u>PEL</u> | |
| Altered Bcl-2 (CHK1/2 substrate) | L R | F | L R | F |
| Altered Bcl-2 (AKT substrate) | R R | | R R | |

(c) Protein Translocation Pathways

Methods of the invention can be used to detect a signaling event that is part of a peptide/protein translocation pathway in order to analyze activities of a kinase of interest in situ and screen for candidate molecules that modulate the kinase in situ. An example of such a translocation pathway is a dual-modal targeting pathway of p450 protein family, in which p450 proteins are targeted to either the endoplasmic reticulum (ER) or the mitochondria.

If a peptide/protein translocation pathway is regulated by a phosphorylation event that takes place on the peptide or protein, the pathway may be engineered to assay the activities of a kinase of interest in place of the wild type kinase that normally regulates the pathway.

Peptide/Protein translocation often requires a sequence in the peptide, i.e., the transporting substrate. That sequence may be called a traffic signaling region, which interacts with transporting proteins to effect translocation among subcellular areas, e.g., intracellular as well as extracellular areas, such as cytosol, cellular organelles, cell surface and extracellular space. The traffic signaling region is analogous to the E3 binding region 11 shown in FIG. 2A, and is the region recognized by a signaling enzyme, in this case, the transporting proteins.

Figure 4:
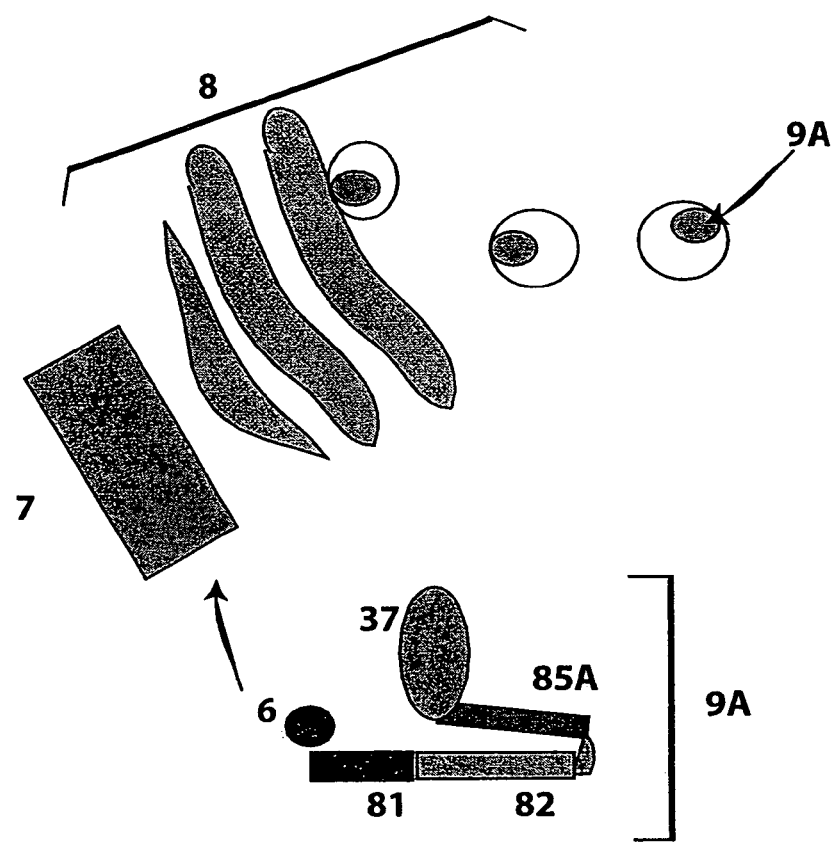
FIG. 4A depicts an embodiment of the invention in which an altered p450, with its mitochondria-targeting region inactivated, is transported into the ER and the secretory pathway.
FIG. 4B depicts the altered p450 of FIG. 4A being transported to the mitochondria after the mitochondria-targeting region is activated.
Figure 4:
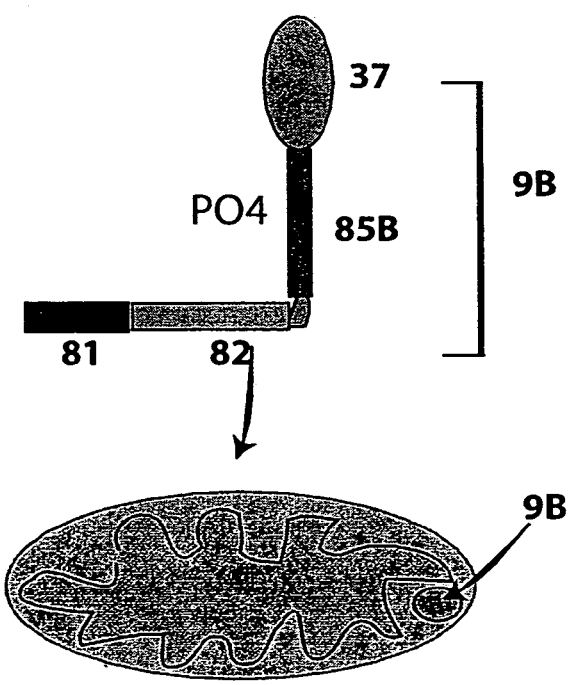

For many members of the cytochrome p450 protein family, for example, a dual-modal targeting pathway has been reported and can be used to illustrate the principle of the invention. Referring to FIG. 4A, like other proteins that target ER, members of the p450 protein family contain an N-terminal hydrophobic sequence, such as a 20-amino-acid region 81 in p450-2B1, which is required for the targeting of the translocation substrate 9A (e.g. a p450-2B1) to the ER 7. The traffic signaling region 81 binds to a signal recognition particle (SRP) 6, which, with an SRP receptor, constitutes a transporting protein that directs the substrate 9A to the membrane of ER 7. The substrate 9A is then transported across the ER membrane and into the secretory pathway 8. Proteins that enter this pathway are delivered to the cell surface and, if they are soluable, to the extra cellular space. Substrate 9A such as p450-2B1, however, also contains a cryptic traffic signaling region 82 that would target the protein to the mitochondria 4. However, under the 9A configuration, the mitochondria-targeting region 82 is masked and inaccessible by transporting proteins. Targeting of substrate 9A to the mitochondria 4 is dependent on the phosphorylation of the serine at position 128 in a kinase recognition domain 85A by cAMP-dependent protein kinase A (PKA). Referring to FIG. 4B, phosphorylation of this residue changes the kinase recognition domain into 85B and also changes the conformation of the substrate into 9B by exposing the cryptic mitochondrial traffic signaling region 82 while inhibiting the binding of the ER traffic signaling region 81 to SRP 6. Phosphorylation at serine 128 thereby shifts targeting of protein 9 from the ER 7 to the mitochondria 4. See H K Anandatheerthavarada et al., *EMBO J.* 18(20): 5494–04 (1999).

To modify an existing peptide translocation pathway for purposes of the invention, the recognition domain for the wild type kinase on the transporting substrate 9 is converted to a domain 85 that is recognized by a kinase of interest without disrupting the phosphorylation-state-dependent function of the traffic signaling regions 81 and 82 of the substrate 9A.

Still referring to FIGS. 4A and 4B, in an exemplary embodiment, the trafficking of substrate 9A is converted from being regulated by PKA phosphorylation to being regulated by a kinase of interest 5 without disrupting effective targeting to mitochondria 4 once phosphorylation of the substrate 9A has taken place. For example, the PKA recognition sequence on p450-2B1 is WKA (123) LRRFS(128) LATM, where the underlined serine at 128 is phosphorylated by PKA. By way of illustration, if AKT is the kinase of interest, an AKT recognition motif RXRXXS may be incorporated into the existing sequence of a p4502B1 by, for example, mutating the alanine at position 123 to an arginine, resulting in a sequence of WKR (123) LRRFS (128) LATM. This mutation transforms the kinase specificity of the substrate 9 from PKA to AKT where the AKT still phosphorylates at the same S (128). The first 160 amino acids of the altered substrate 9B may be fused or otherwise associated with, e.g., at the N-terminus, to a label 37 such as a GFP, beta-galactosidase or alkaline phosphatase, as described in other embodiments. The fusion protein is then expressed in a cell.

Without activation of AKT (e.g., through addition of AKT inhibitor such as wortmanin), the label 37, whether fluorescent or enzymatic, should be detectable in subcellular areas connected by the secretory pathway: the ER, cell surface and extracellular space. The secretion of the label into the extracellular space is especially easy to monitor and the monitoring can be conducted on a real-time basis if the label 37 is, for example, GFP. When AKT is expressed and activated in the cell (e.g., by the addition of insulin), the signal from the label should be detectable in mitochondria instead. If where the label is wild type GFP, emission at 508 nM from secreted protein in extracellular fluid collected, for example, by a robot arm from cells grown in 96, or 384 well plate, can be read using a plate reading fluorimeter. Enzymatic activity can also be read through this format when an enzyme label is chosen. After the reengineered translocation pathway has been shown to be regulated by AKT, the cell may be exposed to candidate molecules such as drug candidates or from a particular library. The candidate molecule's modulatory effects on the modified AKT-regulated pathway may be examined through locations of the signal in the presence of the candidate molecule.

Another embodiment involving a protein translocation pathway is based on phosphorylation mediated regulation of apical targeting of the polymeric Immunoglobulin receptor (pIgR) in epithelial cells.

Trafficking of the pIgR, a type 1 transmembrane receptor that transports dimeric IgA, in epithelial cells has been described as transcytosis. See Cardone et al, *J Cell Biol.* 133(5): 997–1005 (1996). Synthesized pIgR is delivered from the secretory pathway to the basal surface, where it can bind to its ligand, IgA, and then to the apical surface where it is cleaved into the secretory component (the ecto-domain of the pIgR and IgA) and delivered into the apical media. The trafficking of the pIgR to the apical surface is regulated by a phosphorylation of a serine at position 664, proximal to the transmembrane region on the intracellular domain, in a stretch of residues RARHRRNVDRVS (664) IGS. See Casanova et al., *Science* 248(4956): 742–5 (1990). Mutating the serine at position 664 severely inhibits trafficking to the apical surface, indicating that apical targeting is dependent on phosphorylation at that position.

To practice the invention, the kinase recognition region of pIgR is converted to one that is recognized by a kinase of interest without disrupting the phosphorylation-dependent function of the traffic signaling region of pIgR. As a way of illustration, if AKT is the kinase of interest, pIgR's kinase recognition region is converted to contain AKT recognition motif RXRXXS. This may be accomplished by mutating amino acid residues at positions 659 and 661 to arginines, then AKT will phosphorylate at the same S (664). Transcytosis then depends on the activity of AKT. Similar to the previous example, a label 37 may be fused to the modified pIgR to monitor its delivery to the apical surface and secretion of the cleaved form. Effective regulation of the reengineered pathway by AKT can be ascertained through the use of an AKT inhibitor and activator as described in the previous example. The cell may then be exposed to candidate molecules to determine, from the presence or absence of the label in the apical area, any modulatory effect of the candidate molecules on AKT.

Alternatively, the transcytosis may be monitored USING a labeled ligand of the pIgR (e.g., radioactively labeled IgA), AS another embodiment of the label 37. See M. Cardone et al., *J Cell Biol.* 133(5):997–1005 (1996). In this embodiment, epithelial cells expressing the modified pIgR are grown to form tight mono-layers on semi-permeable membrane filters which separate basolateral and apical chambers. The cells are exposed to radio-labeled ligand (IgA) at their basolateral surface. The labeled ligand is excluded from the media in the apical chamber by virtue of the tight junctions in the cell monolayer. However, the label can be delivered to the apical membrane and secreted into the apical media in a complex with the cleaved ecto-domain of the pIgR. See K. E. Mostov et al., *Bioessays.* 17(2):129–38 (1995). The delivery of the radio-labeled ligand is monitored in the collected apical media as indication of transcytosis.

As noted above, the assay is not limited to AKT, other kinases are contemplated by the invention as well. The principle of the invention also applies to other protein translocation pathways including other regulated secretory pathways.

(d) Use of Sequestering Motifs

Another embodiment of the invention provides yet another method of altering a signaling substrate such that its interaction with a signaling enzyme becomes regulated by a phosphorylation event on the substrate. According to this embodiment, a pair of "sequestering motifs" is incorporated into the signaling substrate. The two motifs are respectively disposed on either side of the enzyme-binding region in the signaling substrate. One of the sequestering motifs is a phosphorylation substrate, and its interaction with the other sequestering motif depends on whether the phosphorylation substrate is phosphorylated. The interaction between the two sequestering motifs effectively prevents the signaling substrate from being recognized and bound by a signaling enzyme, which, in turn, prevents the signaling enzyme from being targeted by a signaling pathway in which the signaling enzyme participates. As such, the signaling event between the signaling enzyme and the signaling substrate is successfully modified to be regulated by the kinase that phosphorylates the phosphorylation substrate in the pair of the sequestering motifs. The altered signaling substrate may be further associated with a label. After exposing a cell expressing the labeled signaling substrate to a candidate molecule, it can be determined from changes in the label whether the candidate molecule is capable of modulating the kinase activity in situ.

This embodiment of the invention does not depend on whether the signaling event, in its unaltered state, is regulated by kinase phosphorylation or not. And it may be advantageous that a signaling event where binding between the signaling enzyme and its wild type substrate is not normally (i.e., in its unaltered state) regulated by kinase activity can be modified according to this embodiment to practice the invention. For example, some E3 substrates contain enzyme recognition/binding domains that will be recognized and bound by an E3 ligase and subject to transubiquitination regardless of the phosphorylation state of the E3 substrate. Similarly, some SRP substrates contain traffic signaling regions and are targeted by protein translocation pathways independent of any phosphorylation event.

For example, some E3 substrates contain so-called PEST elements or destruction boxes. A PEST element is a domain enriched in P (Pro), E (Glu), S (Ser), T (Thr) in a negatively charged or neutrally charged background. These sequences can be found in proteins with short half-lives including metabolic enzymes, cell cycle regulating proteins, transcription factors, and certain signaling molecules. See M. Rechsteiner, *Trends Biochem Sci.* 21(7): 267–71 (1996). Removal of these sequences from these proteins such as mammalian G1 regulators cyclin E and cyclin D1 greatly enhances their stability. See K-A Won et al., *EMBO J.* 15:4182–93 (1996); and J A Diehl et al., *Genes Dev.* 11: 957–72 (1997). It has been shown that transfer of the PEST region from mammalian ornathine decarboxylase, a metabolic enzyme that is regulated by 26S proteosome ubiquitin-mediated degradation, to the C-terminus of a reporter protein (e.g., GFP or di-hydrofolate reductase) causes the reporter protein to be degraded at a rate 3 to 5 times faster than that of their wild type counterparts. See P. Corish et al., *Protein Eng.* (12): 1035–40, (1999).

Another example of a phosphorylation-independent E3 recognition/binding region is called a cyclin destruction box. This motif consists of a partially conserved, 9-amino-acid sequence (R(A/T)ALGX(I/V)(G/T)N) where X is any amino acid. The cyclin destruction box is usually located approximately 40–50 amino acid residues from the N-terminus of mitotic cyclins and is necessary for ubiquitination and degradation. See A. Hershko et al., *Annu. Rev. Biochem.* 67: 425–479 (1998). An example of a mammalian destruction box can be found in the G-coupled signaling molecule Rac1 in human endothelial cells. See H N Kovacic et al., *J Biol Chem* 276 (49): 45856–61 (2001). Transfer of the cyclin destruction box to the N-terminus of a reporter protein causes the destabilization of reporter proteins in cell extracts (M. Glotzer et al. *Nature* 349: 132–37, 1991) or in mammalian cells (P. Corish et al., *Protein Eng.* (12): 1035–40 (1999).

Figure 5A:
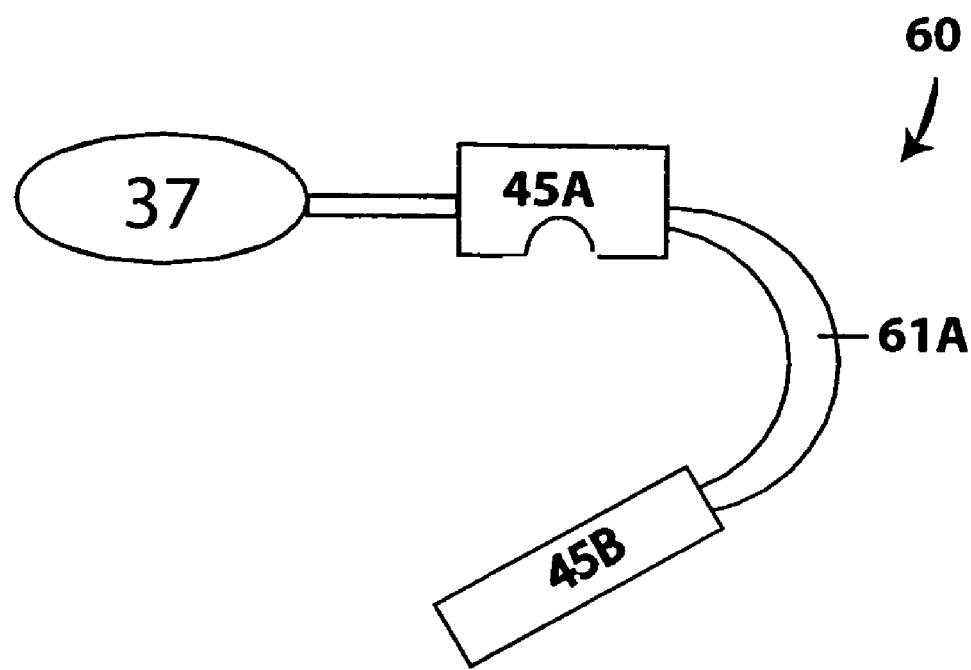
FIG. 5A illustrates a modified signaling substrate containing a pair of sequestering motifs, wherein the sequestering motifs are not interacting with each other, allowing the binding region in the signaling substrate to bind with the signaling enzyme.

Referring to FIG. 5A, in an exemplary embodiment of the invention, a signaling substrate 60 contains a phosphorylation-independent binding region 61A specific for a signaling enzyme. The phosphorylation-independent binding region 61A can be a PEST element, a cyclin destruction box, or a traffic signaling region as described above. The signaling substrate 60 is associated with a label 37 (e.g., GFP). A pair of sequestering motifs 45A and 45B are incorporated into the signaling substrate 60 such that the binding region 61A is flanked by motif 45A on one side and by the other motif 45B on the other side. Motif 45A can be substantially an adapter module such as the RXRXXS-(PO$_4$)XP-binding region from protein 14-3-3, a PDZ domain (named after mammalian Post-synaptic density protein PSD95, Disc large protein of *Drosophila,* and the mammalian tight-junction protein ZO-1), an SH2 domain, an SH3 domain, a WW domain, a PTB domain, and an FHA domain. Sequestering motif 45B is the corresponding kinase-regulated substrate for motif 45A. An example of the motif 45B is a peptide motif RXRXXSXP.

Figure 5B:
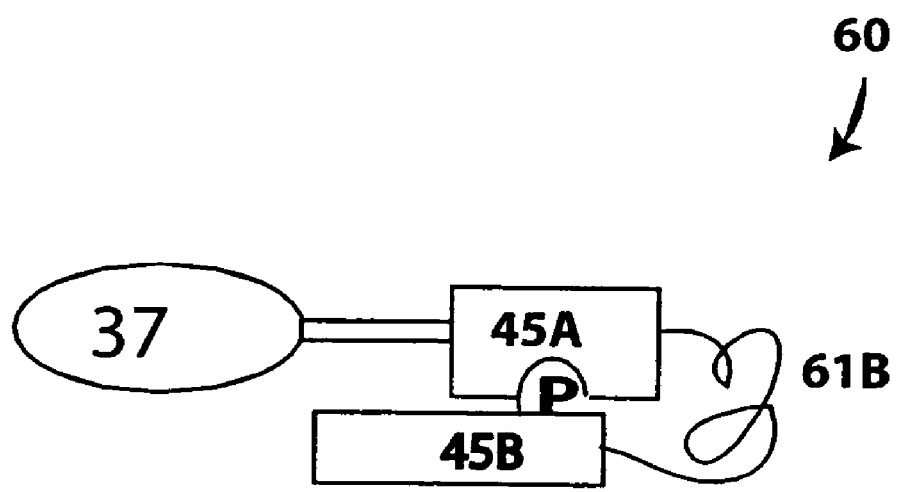
FIG. 5B illustrates the signaling substrate of FIG. 5A wherein the sequestering motifs are interacting with each other, preventing the binding region in the signaling substrate from binding with the signaling enzyme.
Figure 6:
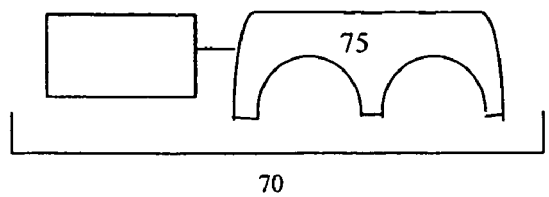
FIG. 6 illustrates an embodiment of the invention in which an adapter module is incorporated into a signaling enzyme.
Figure 6:
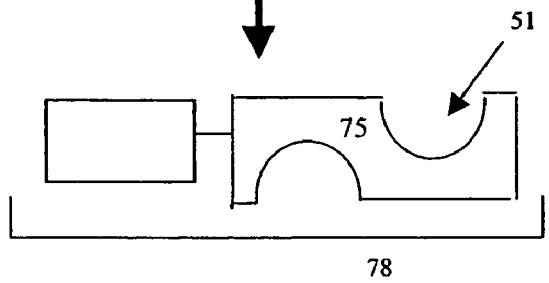
Figure 6:
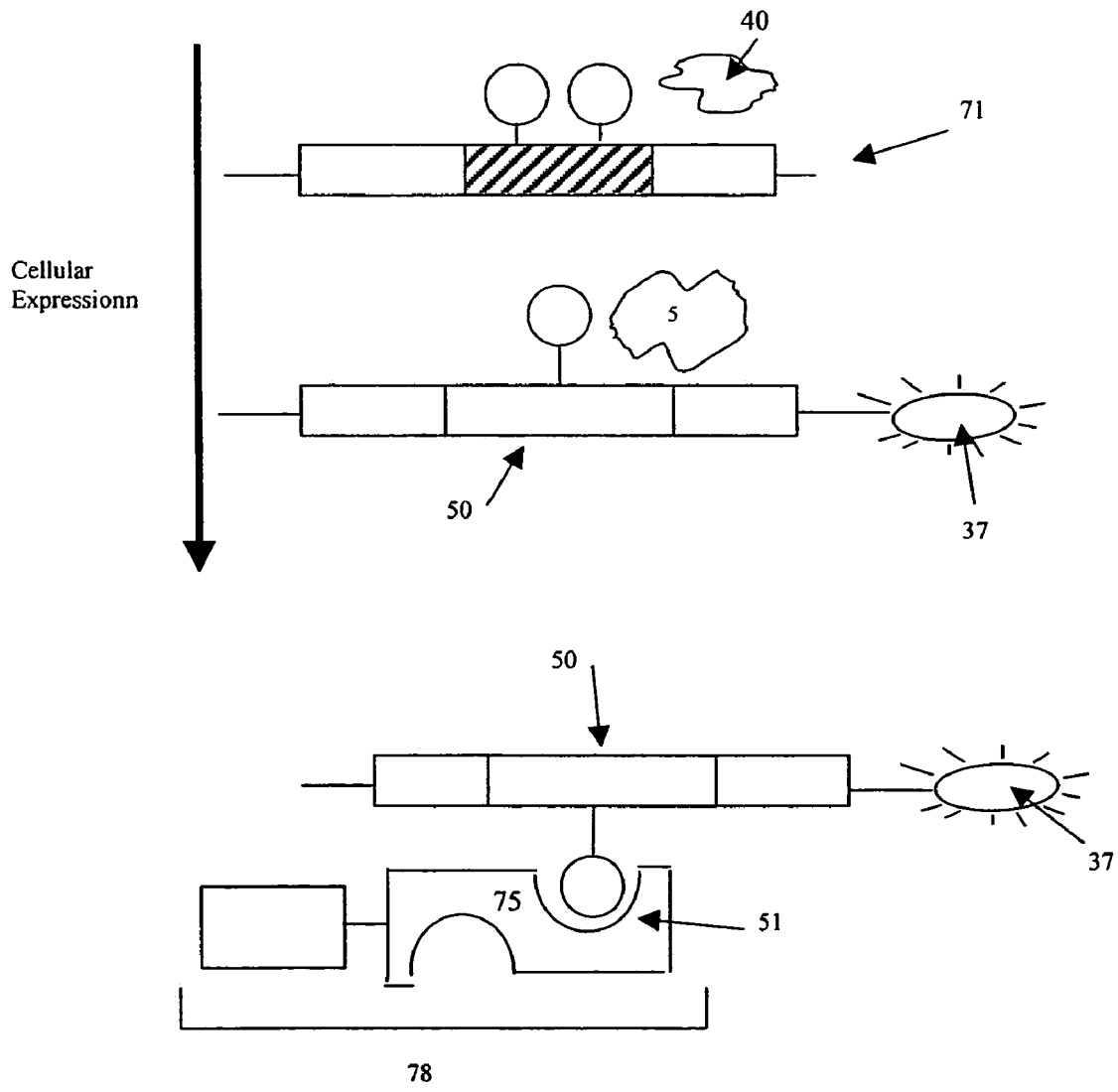

Referring now to FIG. 5B, binding between the sequestering motifs 45A and 45B depends on the specific phosphorylation state of 45B. In some cases, binding takes place when the motif 45B is phosphorylated. In other cases, binding between the motifs 45A and 45B takes place when the motif 45B is de-phosphorylated. Because of the high affinity between motifs 45A and 45B, their binding may cause the binding region 61A to change into the conformation of 61B. Conformation 61B prevents the binding region from being recognized by the signaling enzyme. For example, the binding region 61B may be masked by the sequestering motifs or another portion of the signaling substrate 60. As a result, the signaling substrate 60 is prevented from being targeted by the signaling pathway (e.g., the ubiquitin-mediated degradation pathway or the protein translocation pathway). This can be visualized through signal expression from the label 37. When a candidate molecule modulates the kinase of interest, interaction between the sequestering motifs 45A and 45B may be relaxed and the binding region reverts back to 61A. Once that takes place, the binding region 61A becomes accessible by the signaling enzyme again, causing a change in the expression of the label 37 as the signaling pathway targets both the signaling substrate 60 and the associated label 37. Accordingly, targeting of the signaling substrate 60 by the signaling pathway becomes dependent on the kinase function over the sequestering motif 45B. And the kinase activity can be monitored through the expression of the label 37.

Referring to FIGS. 5A and 5B, as described in previous embodiments, the label 37 is detectable through a signal that has a distinguishable physical or chemical property, including, but not limited to, fluorescence, radioactivity, color, sound, heat, or changes thereof. The label 37 may be associated with the substrate through various ways including, but are not limited to, conjugation, fusion, linkage, or enzymatic interaction. For example, the label 37 may be the enzymatic substrate targeted by a product from the signaling pathway. Expression of the label 37 includes changes in its signal, for example, increase or decrease in the signal intensity, duration or location. An example of such expression is when a fluorescent label is destabilized and degraded, its fluorescence decreasing or disappearing. The label 37 can be used to monitor the signaling event. And since the event is regulated by interaction between the sequestering motif, which, in turn, is regulated by a kinase of interest, label expression becomes indicative of the kinase function.

Referring to FIGS. 5A and 5B, a cell may be transfected to express the altered (i.e., containing the sequestering motifs 45A and 45B) signaling substrate 60 associated with the label 37. When the kinase of interest 5 is expressed (either endogenously, or after transfection, for example), the kinase of interest 5 is able to regulate the phosphorylation state of its phosphorylation substrate 45B, one of the sequestering motifs. As a result, the kinase of interest 5 is able to regulate the binding between the altered signaling substrate 60 and the signaling enzyme. When such binding takes place, the altered signaling substrate 60 and its associated label 37 are targeted by the rest of the components of the signaling pathway. And the targeting can be visualized through the expression of the label 37, e.g., loss of signal in the case of a ubiquitin-mediated degradation.

To identify a candidate molecule capable of modulating an activity of the kinase of interest 5, the transfected cell is exposed to a candidate molecule. For example, if non-interaction between the sequestering motifs 45A and 45B requires phosphorylation of 45B by the kinase of interest 5, that means binding between the signaling enzyme and its substrate 60 and the expression of the label 37, requires activity by the kinase of interest 5. If the candidate molecule has an inhibitory effect on the kinase activity, there should be a change in the expression of the label 37 inconsistent with the activation of the signaling pathway. For example, if the signaling pathway is the ubiquitin degradation pathway, a molecule having an inhibitory effect on the kinase of interest 5 will stabilize the label 37. In other words, if the label 37 remains detectably stable after the cell is exposed to a candidate molecule, it is indicative that the molecule might have an inhibitory effect on the kinase activity of interest. On the other hand, if the candidate molecule has a stimulatory effect on the kinase activity, the destabilization and disappearance of the label 37 due to phosphorylation is detectably enhanced. Further, through quantification of the label 37, by methods known in the art, the modulating effect of the candidate molecule can be quantified.

Interaction between the two sequestering motifs 45A and 45B, takes place on two parts of the same moiety, i.e., the altered signaling substrate 60. As a result, the present embodiment illustrated in FIGS. 5A and 5B may be advantageous in that the interaction is more likely to take place compared to the situation where the inase-regulated interaction requires two separate moieties (e.g., where an adapter module is incorporated into a signaling enzyme while the substrate for the adapter module is on a different protein).

The sequestering motifs 45A and 45B can be incorporated in the signaling substrate 60 at various positions, as long as they are respectively disposed on two sides of the enzyme-binding region 61A in a flanking manner. For example, the sequestering motifs 45A and 45B can be adjacent to the enzyme-binding region 61A. The incorporation of the sequestering motifs 45A and 45B in a flanking manner avoids changing the residues in the enzyme-binding region 61 itself. Therefore, binding between the signaling enzyme and the modified signaling substrate 60 is not likely to be compromised by the incorporation of the sequestering motifs 45A and 45B in the signaling substrate 60. Optionally, there may be any number of amino acid residues serving as a spacer between one of the sequestering motifs, e.g., 45A, and the enzyme-binding region 61. The spacer between a sequestering motif and the enzyme-binding region 61 can be a simple glycine repeat, e.g., 5–30 residues in length, or a more defined structure such as an alpha helix or a short coil. The preferred length of the spacer can be determined through routine experimentation.

II. Altering the Signaling Enzyme

According to the second aspect of the invention, the signaling enzyme participating in a cellular signaling pathway is genetically altered. In its unaltered state, the signaling enzyme does not bind the phosphorylation substrate. In contrast, the altered signaling enzyme is able to bind a phosphorylation substrate of a kinase of interest in a phospho-specific manner. Then, a candidate molecule is exposed to the cell where the altered signaling event takes place. If the candidate molecule changes (e.g., stimulates or inhibits) the signaling event, it is indicative that the molecule may be capable of modulating the kinase activity in vivo. Therefore, through alteration of the signaling enzyme, an in situ signaling event with a characterized readout can be altered many times to screen for drug candidates against a large number of kinases.

(a) Incorporating an Adapter Module in the Signaling Enzyme

Referring now to FIG. 6, in one embodiment of the invention, a cellular signaling pathway is altered by genetically mutating a wild type signaling enzyme 70 to create an altered signaling enzyme 78. The altered signaling enzyme 78 no longer recognizes or binds its wild type phosphorylation substrate 71, but rather recognizes and binds a phosphorylation substrate 50 for the kinase of interest 5. The phosphorylation substrate 50 can include all or a portion of, and preferably, a substantial portion of, a wild type phospho-substrate for the kinase of interest 5. Binding between the altered signaling enzyme 78 and the phospho-substrate 50, and in turn, the targeting of the phospho-substrate 50 by the signaling pathway in which the signaling enzyme 78 participates, depends on the phosphorylation state of the phospho-substrate 50. The phospho-substrate 50 may be part of a larger protein complex, which is also targeted by the same signaling pathway through the above binding. In the particular embodiment shown in FIG. 6, the unaltered signaling enzyme 70 is mutated to contain an adapter module 51, at its substrate-binding region, e.g., the C-terminus 75. But it should be understood that the mutation may occur at other location of the signaling enzyme 70. The adapter module 51 causes the altered signaling enzyme 78 to recognize and bind the phosphorylation substrate 50, and in turn, the protein complex 58, in a phospho-dependent manner.

Genetic mutation of the signaling enzyme 70 to incorporate the adapter module 51 may include the addition, deletion and substitution of one or more amino acid residues in the enzyme 70. For example, SKP1-Cdc53/Cullin-F-box protein (SCF), a type of E3 ligase, has an N-terminus that contains 42–48 amino acid F-box motif which binds to SKP-1, which, in turn, links the protein complex to the E2 enzyme. The carboxy terminus of SCF proteins, on the other hand, has a domain that fits the description of a WD40 motif or a leucine rich repeat that presumably functions as a phospho-serine or phospho-threonine binding module. The WD40 repeat at the carboxy terminus of a class of SCF called Beta-TrCP, for example, binds to its wild type substrate 71 which contains the minimal D(S/T)GXX(S/T) binding region for E3 ligase when both S/T positions (underlined) are phosphorylated. See J T Winston et al., *Curr Biol.* 9(20): 1180–82 (1999). Examples of the wild type substrate 71 include IκB-α, Beta catenin, and the HIV protein VPU. According to the present embodiment of the invention, the WD40 repeat at the carboxy terminus 25 of B-TrCP, an E3 ligase, is modified or mutated to recognize and bind, the phospho-substrate 50 derived from the substrate for a kinase of interest 5 instead of its wild type substrate 10.

Referring again to FIG. 6, once the adapter module 51 is incorporated into the altered signaling enzyme 78, a cell can be transfected to express the altered signaling enzyme 78 and the phospho-substrate 50 associated with a label 37. The label 37, as described in previous embodiments, is able to produce a detectable signal, such as a fluorescent signal or a detectable enzymatic product. The label 37 is associated with the phosphorylation substrate 50, possibly through the protein complex that the phosphorylation substrate 50 is part of. When the kinase of interest 5 is expressed in the cell (e.g., endogenously, or through transfection) and activated (e.g., through provision of kinase activator or provision of a constitutively active version of the kinase), the kinase of interest 5 is able to regulate the phosphorylation state of the phosphorylation substrate 50. In turn, the kinase of interest 5 regulates the recognition and binding of the phosphorylation substrate 50 by the altered signaling enzyme 78. This regulation is detectable through the expression of the label 37, which is associated with the phosphorylation substrate 50 as the signaling pathway targets both. For example, the pathway can be the ubiquitin-mediated degradation pathway or a protein translocation pathway. In the example where the unaltered signaling enzyme 70 is an E3 ligase, the expression of the label 37 is the disappearance of its signal through the degradation of phosphorylation substrate 50 and the associated label 37.

To screen for a candidate molecule capable of modulating an activity of the kinase of interest, the transfected cell is exposed to a candidate molecule. If the expression of the label 37, e.g., the degradation of the label 37 and the resulting loss of signal, changes after exposure to the candidate molecule, it is indicative that the molecule may be modulating the kinase activity of interest. Other aspects of drug screening are similar to those described in previous embodiments.

In a preferred embodiment, the adapter module is at least a portion of an adapter molecule that has been shown to have affinity for, i.e., to recognize and bind to, a wild type phosphorylation substrate of interest in a phosphorylation specific manner. For example, a class of adapter proteins, the 14-3-3 protein family, recognizes the AKT substrate sequence RXRXX(S/T)XP only when the (S/T) is phosphorylated. A narrow monomeric region of the 14-3-3 protein is responsible for the binding. This region consists of basic residues K(49),R(56), Arg(127) and Y(128) that form a positively charged pocket. See M B Yaffe et al. *Curr Opin Cell Biol.* 13(2): 131–8 (2001). Peptides containing this sequence bind phosphorylated AKT substrates in vitro. A region of a signaling enzyme, e.g., the carboxy terminus of an E3 ligase, may be modified to contain the known RXRXXS-(PO$_4$)XP binding region of the 14-3-3 protein. Or, the entire 14-3-3 protein itself may be incorporated into a signaling enzyme through domain swapping, e.g., through swapping with the phosphopeptide-binding region within a wild type E3 ligase. To test if the desired binding region from the adapter protein has been operatively incorporated into a signaling enzyme, a label may be fused to a phosphorylation substrate for a kinase of interest to determine whether the label is successfully targeted by the signaling pathway.

Another example of all or part of an adapter protein incorporated in a signaling enzyme 70 such as an E3 ligase, involves the incorporation of domains such as the src homology 2 (SH2) domain into a signaling enzyme 70. Adapter proteins containing SH2-type domain recognizes peptide sequences that contain a phosphorylated tyrosine residue, usually within 3 to 6 residuals to the carboxy terminal. These peptide sequences are often found within the cytoplasmic portion of receptor tyrosine kinases (RTK), including growth factor cytokine receptors EGF, FGF, Erb-2, and PDGF. See T Pawson et al., *Genes and Development*, vol. 14, No.9, pp. 1027–1047 (2000). Activation of these receptors leads to autophosphorylation on specific tyrosines, which allows binding of adapter proteins that contain the SH2 domains. The SH2 domain links the activated RTKs to downstream signaling molecules, and serve key functions in intracellular signal transduction.

Figure 7A:
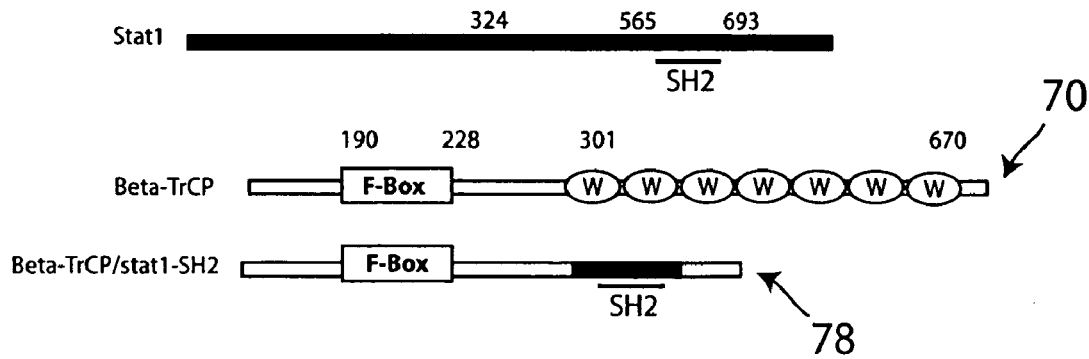
FIG. 7A depicts an embodiment of the invention, a modified E3 ligase (Beta-TrCP) in which an SH2 domain from Stat 1 is incorporated.

An SH2 domain consists of approximately 100 amino acids that form part of a ligand binding surface. See M. J. Eck et al., *Nature* 362: 87–91 (1993). SH2 domains are found in a range of signaling molecules including PLC gamma, Grb-2, the signal transducers and activators of transcription (Stat) proteins, and Src. FIG. 7A shows the locality of an SH2 domain in Stat 1. The SH2 domain can be inserted into a host protein and maintain specific binding to phosphotyrosine-containing ligand, as demonstrated using the Stat3 SH2 domain. See U. Hemmann et al., *J. Biol. Chem.*, 31: 271(22): 12999–13007 (May, 1996). In an embodiment of the invention, an SH2 domain is inserted into the signaling enzyme 70, converting the signaling enzyme to recognize a phosphotyrosine-containing SH2 ligand, e.g., RTK. To illustrate, FIG. 7A also shows that an SH2 domain from Stat1 is swamped with a tryptophan (W) rich region in an E3 ligase, Beta-TrCP. The resulting E3 ligase is denoted as Beta-TrCP/Stat1-SH2. Upon phosphorylation of the tyrosine in the SH2 ligand, E3 ligase mediated ubiquitination and degradation of the SH2 ligand follows. By associating a label, such as GFP, with the intracellular portion of the selected SH2 ligand, the activity of the kinase can be monitored as described above in previous embodiments.

Figure 7B:
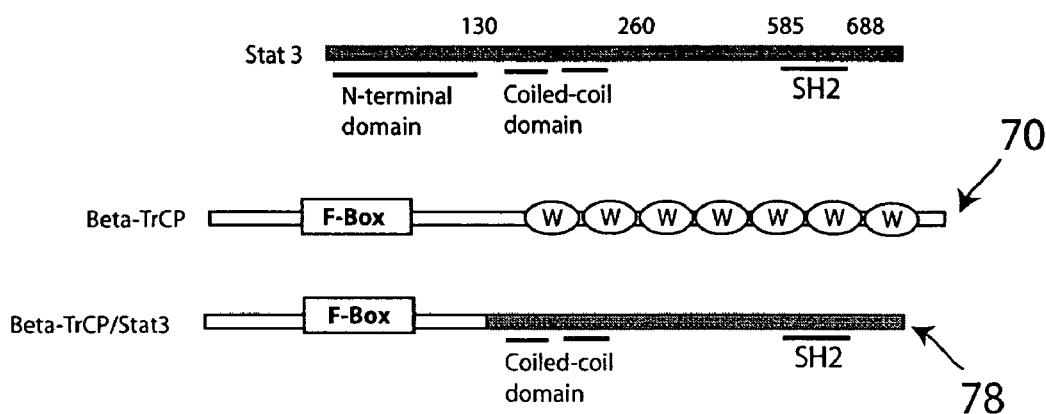
FIG. 7B depicts an embodiment of the invention, a modified E3 ligase (Beta-TrCP) in which an SH2 domain from Stat 3 is incorporated.

Some portion of the adapter protein other than the ligand binding region may be incorporated into the signaling enzyme 70 for proper recognition and binding of the ligand. Referring to FIG. 7B, a so-called "coiled-coil domain" in Stat 3 is needed for the proper function of the SH2 domain and is also incorporated into the E3 ligase, Beta-TrCP, through swapping with the tryptophan (W) rich region. The resulting altered E3 ligase is denoted as "Beta-TrCP/Stat3." Other linkers useful for the proper function of the ligand binding region may be determined through routine experiment.

Figure 7C:
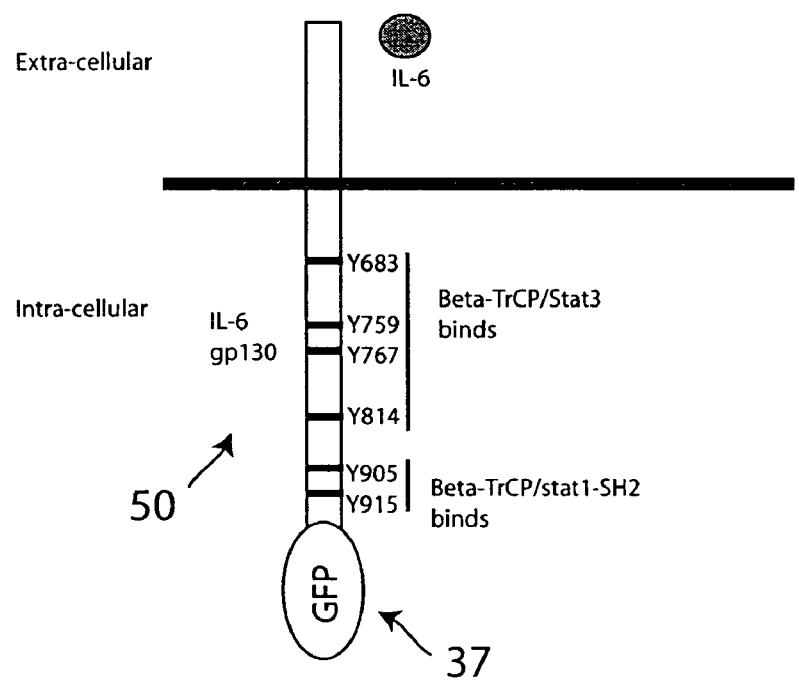
FIG. 7C illustrates an embodiment of the invention in which the modified E3 ligase shown in FIGS. 7A and 7B bind to gp130 after activation by IL-6 growth factor.

Referring to FIG. 7C, in a preferred embodiment, the IL-6 growth factor receptor (gp130) is used as the ligand for SH2. Gp130 binds to the SH-2 domain of the Stat-1 protein when either tyrosines in two "YXPQ" motifs, Y(905)LPQ or Y(915)MPQ, is phosphorylated by the gp 130-associated kinases JAK1, JAK2, or TYK2. The binding specificity of SH2 for gp130 has been shown to be portable in swapping experiments involving Stat-1's SH2 domain, i.e., the SH2 domain from Stat 1 can be inserted into a protein of interest so that the protein of interest binds IL-6 growth factor receptors. See U. Hermmann et al., *J. Biol. Chem.*, 31: 271(22): 12999–13007 (May, 1996). According to this embodiment of the invention, the Stat1 SH2 domain is inserted into the C terminal of the beta-TrCP E3 ligase by mutating, deleting or adding specific amino acid residues. Similarly, the SH2 domain from Stat3 is also portable, and can be incorporated into a Beta-TrCP as shown in FIG. 7B. A label 37, e.g., GFP, is associated with the phosphorylation substrate 50, in this case, gp130.

Exposure to the IL-6 growth factor activates gp130 and causes phosphorylation by the gp130-associated kinases JAK1, JAK2, or TYK2 on the requisite tyrosines on gp 130 for binding with the SH2 domain to take place. Once gp130 is phosphorylated, the altered Beta-TrCP, which has the SH2 domain, binds gp130 and targets gp130 to the ubiquitin-mediated degradation pathway. The destabilization of gp130 or modulation thereof by a drug candidate is monitored through the loss of the signal from the label 37. Note that while both Beta-TrCP/Stat1-SH2 and Beta-TrCP/Stat3 are shown in FIG. 7C as bound to gp130, only one of the altered Beta-TrCP is need for the assay.

Further examples of adapter modules 51 that can be used to convert a signaling enzyme, e.g., an E3 ligase, to recognize other phosphorylation substrates of interest include sequence specific binding domains such as SH3 domains, WW domains, PTB domains and FHA domains. Recognition of a ligand by some of these domains, for example, SH3, is regulated by a kinase in the sense that the domain will recognize the ligand when the ligand is not phosphorylated, and will not bind the ligand only when it is phosphorylated.

(b) Other Ways of Altering the Signaling Enzyme

In addition to incorporating the adapter module 51, there are other ways of altering the wild type signaling enzyme 70, preferably by altering its substrate-binding region, to recognize and bind a phosphorylation substrate 50 regulated by a kinase of interest 5.

For example, in a preferred embodiment, random mutagenesis is carried out on the substrate-binding region, e.g., the carboxy terminus 75 of an E3 ligase, of a signaling enzyme 70 responsible for a signaling event. Again, examples of the signaling enzyme 70 include, but are not limited to, an E3 ligase and a transporting protein. And it does not matter whether the signaling event, in its unaltered state, is regulated by phosphorylation or not. The mutated signaling enzyme 78 is screened for optimal binding to the kinase-specific substrate of interest 50. An example of kinase-specific substrate of interest 50 is a peptide with the RXRXX(S/T) sequence where the amino acid that can be either S or T is phosphorylated. This sequence is the consensus recognition motif for AKT.

The in situ screen for selecting and characterizing mutant signaling enzyme 78 that binds to a specific phosphorylation substrate 50 may be performed on a high-density multiplexed protein array. For example, individual clones of various mutant signaling enzyme 78 derived from a random mutagenesis protocol, or another method such as error prone PCR, are arrayed on a fixed substrate and selected for phosphopeptide specific binding. The selected clones are then characterized by, for example, nucleic acid sequencing, in vitro measurements of binding affinity using standard biochemical and biophysical techniques (e.g., isothermal titration calorimetry, surface plasma resonance, and fluorescence polarization anisotropy). A variety of other techniques are also available to identify these optimized altered phosphopeptide binding regions including high-throughput screening using phage-displayed mutant signaling enzyme 78 selected for binding to immobilized phosphorylation substrate 50, or affinity capture of the mutant signaling enzyme 78 using phosphorylation substrate 50 immobilized on micro-beads.

To verify that the mutant signaling enzyme 78 with a modified substrate binding region binds in situ to the phosphorylation substrate 50 subject to the regulation by the kinase of interest 5, the mutant signaling enzyme 78 may be cloned into an expression vector and co-transfected with a labeled phosphorylation substrate 50 of one particular phosphorylation state (i.e., phosphorylated or non-phosphorylated). The desired mutation is confirmed when the signal from the label, e.g., fluorescence, is targeted by the signaling pathway as expected. For example, if the signaling pathway is the ubiquitin-mediated degradation, the signal should disappear, suggesting that the labeled phosphorylation substrate 50 has been recognized by the E3 ligase, transubiquitinated, and degraded by the proteosome. A negative control substrate can be the same phosphorylation substrate 50 having the opposite phosphorylation state and with the same label.

To confirm that a labeled test phosphorylation substrate 50 is of a particular phosphorylation state in vivo, the labeled test substrate may be initially recovered from cell extracts using an antibody specific for the label. The immunoprecipitated peptide can then be analyzed for its phosphorylation state using phosphorylation specific anti-motif antibodies on a western blot or in affinity capture mass spectrometry. These antibodies are commercially available for many kinase substrates or can be made using standard protocols known to one skilled in the art. To confirm that the observed expression of the label, e.g., signal degradation, depends upon activation by a kinase of interest, negative control experiments can be conducted. Examples of such negative controls include co-transfecting cells with dominant negative mutant of the kinase of interest, or by treating the cells with specific kinase inhibitors where such inhibitors are known.

As described in detail in connection with other embodiments, the label 37 should be able to produce a detectable signal, such as a fluorescent signal or a detectable enzymatic product. Examples of the label 37 include, but are not limited to, fluorescent proteins (e.g., GFP) or enzymes (e.g., beta-galactosidase).

III. Multiplexing

According to one aspect of the invention, the study of kinase activity using one of the reengineered cellular pathways can be multiplexed to study multiple kinases. For example, different versions of E3 ligase may each be mutated to recognize phosphorylation peptides derived from different kinase substrates. When each of these different versions of E3 ligase is fused to a distinct label, they can be assayed in the same cell to study simultaneously different kinase activities including a candidate molecule's modulatory effects on mulitiple kinases. A distinct label is contemplated here to be capable of giving off a signal distinguishable from those from other labels. Examples of such labels include modified GFP proteins that emit fluorescence at distinct wavelengths, such as YFP and CFP and enzymes that produce different colorometric readouts.

Different altered signaling substrates (e.g., altered E3 substrate 30) can be constructed to be recognized by several different kinases. Similarly, each of these fusion proteins may be fused to a distinct label 37. These fusion proteins may be used in accordance with the invention, for example, either in a ubiquitin-mediated pathway or a translocation pathway as described above. Expressing these proteins in a single cell allows the simultaneous in situ analysis of modulating several kinases.

The multiplexing aspect of the invention can be used to study compound specificity with regard to multiple kinases in situ. Unlike previous approaches where one particular kinase interaction is isolated and studied, the invention provides a method where multiple kinase interactions are studied in a complex similar to that found in their natural cellular environment. A drug development program in accordance with the invention will provide information not only on drug (e.g. kinase inhibitors) specificity with regard to several kinases, but also on drug specificity when these kinases are interacting with each other in vivo. In view of frequent reports of the lack of specificity of kinase inhibitors in vivo, for example, S. P. Davies et al., *Biochemical J.* 351 (Pt 1): 95–105 (2000), the possibility of simultaneous in situ study of complex cellular interactions becomes especially valuable. For example, to develop an inhibitor drug for a particular kinase, the multiplexing aspect of the invention can be used to study in vivo specificity of the drug against that particular kinase while monitoring its effects on other kinases within the same cell.

One powerful multiplexing application is in situ mapping of kinase pathway epistasis. As an example, a drug candidate's effect on several kinases in a linear pathway can be studied simultaneously to determine the drug's efficacy as a pathway blocker, and to determine whether parallel activation pathways should be considered when trying to inhibit that cell signaling pathway.

IV. Selection of Compound Libraries

Whichever cellular system is chosen, e.g., a degradation pathway or a translocation pathway, chemical libraries provided by commercial sources, including a focused library of candidate molecules may be used to perform cell-based screening in accordance with the invention. An example of a focused library specific for kinase inhibitors is a 2,6,9-trisubstituted purine library. See P. Shultz, *Science* 281: 533–538, (1998) and Y, T. Chang et al., *Chem Biol,* 6:361–375 (1999).

One approach to designing a candidate molecule for the screening is to use structural information of the target to design molecular attributes that will help binding to the target. The target may be, e.g., the kinase of interest or its substrate. In one embodiment, structure of the kinase substrate is used to guide the selection/synthesis of the library to be screened. The optimized conversion sequences may be used as a starting point to determine structure of an inhibiting molecule.

Various computational programs and software may be used for designing candidate molecules for screening. Examples include the DOCK program developed by at the University of California in San Francisco. The DOCK program applies knowledge of the three-dimensional structure of the target to rational drug design.

In another embodiment, libraries with large amount of complexity are used for the screening. An example of such a library is described as the Ugi reaction. See S. Schrieber et al., *Science* 97: 1964–1969 (2000).

As a first pass these molecules may be screened for their ability to bind to the kinase of interest. In yet another embodiment of the invention, monomeric low affinity binders identified through the first pass may be cross-linked and rescreened for higher affinity. In the linked complex, each molecule may contribute potency and selectivity to modulate the kinase of interest. For example, linked molecules may bind to distinct regions of the kinase. See D J. Maly et al., *PNAS* 97:2419–2424 (2000).

V. Clinical Applications

The screening methods in accordance with the invention may be used to test and design drugs with various clinical applications. Such applications include anti-inflammatory candidate molecules. Examples of these molecules include those that inhibit IKK and thereby inhibit the degradation of IκBα and the activation of NFkB. The invention, for example, can be used to modify the amino acid sequence surrounding the IKK recognition sequence so that it allows rational drug design as described above.

In another embodiment, the invention is useful in the area of anti-tumor therapeutics, and immune response regulating drugs. For example, the target kinase can be AKT which functions as a survival kinase that regulates apoptosis inducing proteins, caspase 9, Bad, and the transcription factor Forkhead. See M H Cardone et al., *Science,* 282 (5392): 1318–21 (1998); and S R Satta et al, *Genes Dev.* 13 (22): 2905–27 (1999). Anti-ischemia drugs can also be developed using the methods of the invention by targeting pro-apoptotic kinases such as JNK and Ask1. Such anti-ischemia drugs are useful for treating atherosclerosis.

The content of all documents, patents, publications cited above in the specification are herein expressly incorporated by reference to the extent applicable. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the invention.

We claim:

1. A fusion protein comprising a genetically altered signaling enzyme;

said signaling enzyme producing a downstream signal and comprising an E3 ubiquitin ligase (E3 ligase), said alteration producing an adapter module in said signaling enzyme capable of binding to a phosphorylation substrate that said enzyme does not bind in its unaltered state, said binding being regulated by a kinase of interest, and said kinase regulation being detectable through a change in said signal.

2. The fusion protein of claim 1 wherein said module is disposed at the carboxy terminus of said E3 ligase.

3. The fusion protein of claim 1 wherein said E3 ligase is an SKP1-Cdc53/Cullin-F-box protein (SCF).

4. The fusion protein of claim 3 wherein said SCF is a TrCP.

5. A fusion protein comprising a genetically altered signaling enzyme;

said signaling enzyme producing a downstream signal and comprising a transporting protein comprising a cytochrome p450 protein, said alteration producing an adapter module in said signaling enzyme capable of binding to a phosphorylation substrate that said enzyme does not bind in its unaltered state, said binding being regulated by a kinase of interest, and said kinase regulation being detectable through a change in said signal.

* * * * *